(12) United States Patent
Canning et al.

(10) Patent No.: US 6,979,442 B1
(45) Date of Patent: Dec. 27, 2005

(54) STABILIZED PROTEIN COMPOSITIONS

(75) Inventors: Peter C. Canning, Terre Haute, IN (US); Barbara J. Kamicker, Niantic, CT (US); Kasra Kasraian, Pawcatuck, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 09/372,917

(22) Filed: Aug. 12, 1999

Related U.S. Application Data

(60) Provisional application No. 60/096,876, filed on Aug. 17, 1998.

(51) Int. Cl.$^7$ .................. A61K 45/00; A61K 38/00; C07K 17/00

(52) U.S. Cl. .................. 424/85.1; 424/134.1; 424/810; 514/2; 514/12; 514/885; 514/921; 530/350; 530/351

(58) Field of Search ............................ 424/85.1, 134.1, 424/810; 514/12, 2, 885, 921; 530/350, 351

(56) References Cited

U.S. PATENT DOCUMENTS

| | | | |
|---|---|---|---|
| 4,623,717 A | 11/1986 | Fernandes et al. | |
| 4,645,830 A | 2/1987 | Yasushi et al. | |
| 4,647,454 A | 3/1987 | Cymbalista | |
| 4,675,184 A | 6/1987 | Hasegawa et al. | |
| 4,810,643 A | 3/1989 | Souza | |
| 4,833,127 A | 5/1989 | Ono et al. | |
| 4,992,271 A | 2/1991 | Fernandes et al. | |
| 5,104,651 A * | 4/1992 | Boone et al. | 424/85.1 |
| 5,290,764 A * | 3/1994 | Duke, Jr. et al. | 514/21 |
| 5,366,964 A | 11/1994 | Lindstrom et al. | |
| 5,472,857 A | 12/1995 | Boone et al. | |
| 5,503,827 A * | 4/1996 | Woog et al. | 424/85.1 |
| 5,567,677 A | 10/1996 | Castensson et al. | 514/12 |
| 5,580,856 A | 12/1996 | Prestrelski et al. | |
| 5,606,024 A | 2/1997 | Boone et al. | |
| 5,661,125 A | 8/1997 | Strickland | 514/8 |
| 5,681,814 A | 10/1997 | Clark et al. | 514/12 |
| 5,696,086 A | 12/1997 | Avraham et al. | 514/12 |
| 5,747,447 A | 5/1998 | Swift et al. | 514/9 |

FOREIGN PATENT DOCUMENTS

| | | | |
|---|---|---|---|
| EP | 0080879 | | 6/1983 |
| EP | 0612846 | | 8/1994 |
| EP | 0719860 | | 7/1996 |
| GB | 2 193 631 A | * | 2/1988 |
| GB | 2193631 A | * | 2/1988 |
| NZ | 259333 | | 12/1992 |
| NZ | 268441 | | 6/1993 |
| NZ | 271873 | | 8/1993 |
| WO | 8604506 | | 8/1986 |
| WO | 8604606 | | 8/1986 |
| WO | 8702060 | | 4/1987 |
| WO | 9414466 | | 12/1993 |

OTHER PUBLICATIONS

Hammond et al., Blood (1990) 76(3):523-532.*
Lovejoy et al., Journal of Molecular Biology (1993) 234(3): 640-653.*
Gietz et al, Sustained release of injectable zinc-recombinant hirudin suspensions: development and validation of in vitro release, Eur. J. Pharamceutics and Biopharmaceutics (May 1998) 45(3):259-64.*
Lovejoy et al., Journal of Molecular Biology, vol. 23, No. 3, pp. 640-653, 1993.*
Calibiochem, "Buffers: A guide for the preparation and use ofbuffers in biological systems," Edited by Donald E. Gueffroy, Calbiochem-Behring Corp, Fourth printing, pp. 1-24, 1981.such features (i.e., methods of increasing effect of immune response to patho.*
Nagata, et al.; Nature; vol. 319; pp. 415-418; Molecular cloning and expression cDNA for human granulocyte colony-stimulating factor; (1986).

* cited by examiner

*Primary Examiner*—Jon Weber
*Assistant Examiner*—Abdel A. Mohamed
(74) *Attorney, Agent, or Firm*—Thomas A. Wootton; Kenneth I. Kohn; Kohn & Associates, PLLC

(57) ABSTRACT

This invention relates to stabilized protein compositions, methods for preparing such stabilized protein compositions, dosage forms for administering such stabilized protein compositions to mammals and methods for preventing or treating infections in mammals by administering such protein compositions to mammals. More particularly, the stabilized protein compositions of the present invention contain therapeutically effective amounts of G-CSF, such as bovine G-CSF, in combination with a stabilizing buffer, such as HEPES, TES or TRICINE, for treating and preventing infections, including mastitis, in cattle.

18 Claims, 17 Drawing Sheets

STABILIZED PROTEIN COMPOSITIONS

This application claim the benefit of provisional application No. 60/096,876 filed Aug. 17, 1998.

FIELD OF THE INVENTION

This invention relates to stabilized protein compositions. The stabilized compositions of the present invention are useful in delivering therapeutically effective amounts of proteins, including colony stimulating factors, such as bovine granulocyte colony stimulating factor (bG-CSF), to mammals, including humans, cattle, swine, horses, goats, sheep, dogs and cats, for sustained periods. More particularly, the stabilized compositions of the present invention contain stabilizing buffers such as HEPES, TES and TRI-CINE are capable of maintaining a sustained period of protein activity, both in vivo and in vitro.

BACKGROUND OF THE INVENTION

Formulations of therapeutically effective proteins, such as G-CSF, remain difficult to formulate for extended shelf life in vitro and in vivo activity. Formulations of such proteins must maintain their activity and biological integrity for appropriate periods of time for effective treatment. In addition, formulations of such proteins must be manufacturable as well as capable of being administered to an animal in a pharmaceutically acceptable manner.

Pharmaceutical compositions of proteins have been provided in frozen or lyophilized form and maintained in vitro under storage conditions, which maintain protein activity for extended periods of time. Lyophilized preparations are reconstituted prior to use with pharmaceutically acceptable diluents, such as sterile water for injection. Pharmaceutical compositions of proteins have also been provided in liquid form. Such liquid protein formulations are difficult to maintain in storage due to the loss of protein activity over time, particularly at elevated temperatures.

Formulations of therapeutically effective proteins, whether in solid (lyophilized) or liquid form, are difficult to administer to animals without sudden loss of activity after administration, such as by subcutaneous injection, to the animal. Rapid loss of protein activity at the injection site renders the protein inconvenient for treating infections in mammals since effective therapy requires daily doses during desired periods of coverage. Granulocyte colony stimulating factors (G-CSFs), such as bovine granulocyte colony stimulating factor (bG-CSF), are unstable at or above 40° C. due to loss in secondary structure and disulfide interchange and subsequent loss in activity. This loss in activity occurs at the injection site since bovine body temperature is around 40° C. and the injection site is at physiological pH range.

Various protein formulations for extending shelf life are known. U.S. Pat. No. 5,104,651, issued Apr. 14, 1992 (Boone et al.), refers to a pharmaceutical composition of G-CSF and an acid at a pH in the range of 3.0–3.7 with a conductivity of less than 1000 μmhos/cm. U.S. Pat. No. 4,992,271, issued Feb. 12, 1991 (Fernandes et al.), refers to a pharmaceutical composition containing a biologically active recombinant interleukin 2 protein dissolved in an aqueous based carrier medium at a pH of 6.8 to 7.8 and which further contains a stabilizer for the protein, such as human serum albumin. U.S. Pat. No. 4,623,717, issued Nov. 18, 1986 (Fernandes et al.), refers to pasteurized therapeutically active protein compositions whereby thermally sensitive, therapeutically active proteins are pasteurized by mixing the protein with a stabilizing amount of a sugar or reduced sugar and an amino acid prior to pasteurization. U.S. Pat. No. 4,645,830, issued Feb. 24, 1987 (Yasushi et al.), refers to a stable interleukin 2 composition containing interleukin 2, human serum albumin and a reducing compound, at a pH of 3 to 6 in solution. U.S. Pat. No. 4,647,454, issued Mar. 3, 1987, (Cymbalista), refers to a method of stabilizing human fibroblast interferon with polyvinyl pyrrolidone. U.S. Pat. No. 4,675,184, issued Jun. 23, 1987 (Hasegawa et al.), refers to a pharmaceutical composition for treating viral infections containing interferon, a tri or higher polyhydric sugar alcohol, an organic buffer and a pharmaceutical carrier or diluent, wherein the composition has a pH of about 3 to 6. All of the aforementioned references are incorporated by reference in their entirety.

One example of a therapeutically effective class of proteins is that of granulocyte colony stimulating factors (G-CSFs). Granulocyte colony stimulating factor (G-CSF) is one of several glycoprotein growth factors known as colony stimulating factors. Such colony stimulating factors support the proliferation of haemopoietic progenitor cells and stimulate proliferation of specific bone marrow precursor cells and their differentiation into granulocytes. In addition, G-CSF is capable of stimulating neutrophilic granulocyte colony formation and to inducing terminal differentiation of murine myelomonocytic leukemic cells in vitro. G-CSF has also been shown to stimulate the functional activities of neutrophils resulting in enhanced microbiocidal activity. G-CSF has a known amino acid sequence of 174 amino acids.

Recombinant forms of CSFs and G-CSFs have been prepared. The cloning and expression of DNA encoding for human G-CSF is known (Nagata, S. et al., Nature, 319, 415–418 (1986). WO-A-8604606 and WO-A-8604506 describe a gene encoding human G-CSF. U.S. Pat. No. 5,606,024, issued Feb. 25, 1997 (Boone et al.) and U.S. Pat. No. 5,472,857 issued Dec. 5, 1995, describe the DNA sequence encoding canine granulocyte colony stimulating factor (cG-CSF) as well as a method for treating or preventing infections in canine or feline animals by administering effective amounts of human and canine G-CSF to such animals. U.S. Pat. No. 4,810,643, issued Mar. 7, 1989 (Souza), describes human G-CSF like polypeptides. European Patent Application No. 719 860, published Jul. 3, 1996, describes the amino acid sequence of naturally occurring bovine granulocyte colony stimulating factor (bG-CSF), the DNA sequence encoding for bG-CSF and a method for treating or preventing mastitis in an animal by administering to the animal an effective amount of G-CSF. WO-A-8702060 describes human G-CSF like polypeptide, sequences encoding them and methods of producing them. U.S. Pat. No. 4,833,127, issued May 23, 1989 (Ono et al.), describes a novel biologically active human granulocyte colony stimulating factor. European Patent Application No. 612 846, published Aug. 31, 1994, describes certain G-CSF analogs and compositions containing such analogs. All of the aforementioned references are incorporated by reference in their entirety.

Granulocyte colony stimulating factors are useful as anti-infective agents which increases the immune competence of the animal rather than targeting a specific microbial target necessary for growth or virulence. There are few other commercially available agents used in veterinary medicine that target non-specific immune responses leading to increased resistance to microbial infection. Available control measures are limited to conventional antimicrobials and a limited number of biologicals. Economic losses associated with milk withdrawal periods in cattle limit the utility of conventional antimicrobials. Current vaccines target a limited number of species and the field efficacy of these agents vary widely. The most successful vaccines, (*E. coli* J5) are limited in their world wide use due to safety concerns associated with endotoxin contamination.

Mastitis is a major disease problem affecting dairy producers worldwide. Economic losses in the United States associated with mastitis exceed $1 billion annually. These losses are associated with mortalities, milk discard, acute and chronic decreases in milk production, increased early culling and drug and veterinary labor expenses. Periparturient dairy cows exhibit impaired immune responsiveness (neutrophil function) which increase their susceptibility to bacterial infections of the mammary gland. The impact of this increased susceptibility is exemplified by the fact that about 40% of new clinical intramammary infections occur within the first two weeks after calving. Mastitis is associated with a wide variety of bacterial pathogens including both Gram positive and Gram negative organisms. Some of the known pathogenic microorganisms causing mastitis are *Escherichia coli, Staphylococcus aureus, Streptococcus agalactiae, Streptococcus uberis, Streptococcus dysgalactiae, Aerobacter aerogenes, Klebsiella pneumoniae* and *Pseudomonas aeruginosa*. These pathogens enter the udder through the test canal and produce inflammation of the milk producing tissue causing the formation of scar tissue, which can result in a permanent loss of milk producing capacity. Various forms of mastitis include: udder infection, chronic mastitis, clinical mastitis and subclinical mastitis.

Current antimicrobial therapies and vaccines possess a number of deficiencies that limit their utility in lactating cows. Antibiotic therapy to control mastitis has been found lacking. There is a need for a biotherapeutic agent, which is useful in restoring normal immune competence resulting in the decreased incidence and severity of mastitis.

Bovine respiratory disease, also referred to as shipping fever, is another common disease affecting cattle. Bovine respiratory disease affects cattle after shipment either into feedlots or onto pasture and results from a variety of stresses affecting cattle including weaning, castration, dehorning, fasting, overcrowding, exposure to infectious agents, diet changes and temperature changes, in combination with infection by any of several known pathogens. *Pasteurella haemolytica* is one such common pathogen resulting in damage to the respiratory system of cattle.

Several additional infectious diseases, including various reproductive diseases, are also known to affect humans, swine, cattle, dogs, cats, horses, goats and sheep. One example of such a disease, occurring in cattle, is metritis.

There is a need for a stable protein composition which remains therapeutically effective for sustained periods of time in vivo. In addition, there is a need for formulations of proteins that provide for extended in vitro shelf life and storage.

SUMMARY OF THE INVENTION

The present invention relates to a stabilized protein composition comprising a protein and a stabilizing buffer, which composition is capable of maintaining therapeutic levels of such protein for a sustained period.

Specific embodiments of the invention include a stabilized protein composition which composition is at a physiological pH.

Other specific embodiments of the invention include a stabilized protein composition which composition is at a physiological temperature.

Other specific embodiments of the invention include a stabilized protein composition wherein the stabilizing buffer is selected from the group consisting of: HEPES, TES and TRICINE.

Still other specific embodiments of the invention include a stabilized protein composition wherein the sustained period is at least about three days.

Still other specific embodiments of the invention include a stabilized protein composition wherein the protein is selected from the group consisting of: colony stimulating factors, somatotropins, interleukins, interferons, cytokines, antibodies and antigens.

More specific embodiments of the invention include a stabilized protein composition wherein the protein is selected from the group consisting of: human G-CSF, bovine G-CSF and canine G-CSF.

More specific embodiments of the invention include a stabilized protein composition wherein the protein is G-CSF and wherein the G-CSF is present at a concentration in the range of 0.01 to 5 mg/ml.

Other specific embodiments of the invention include a stabilized protein composition wherein the protein is G-CSF and wherein the stabilizing buffer is selected from the group consisting of: HEPES, TES and TRICINE.

Other more specific embodiments of the invention include a stabilized protein composition wherein the protein is G-CSF and wherein the stabilizing buffer is present in a concentration ranging from about 0.05M to about 2M.

Still other specific embodiments of the invention include a stabilized protein composition wherein the protein is G-CSF and wherein the composition is at a physiological pH.

Still other specific embodiments of the invention include a stabilized protein composition wherein the protein is G-CSF and wherein the composition is at a physiological temperature.

More specific embodiments of the invention include a stabilized protein composition wherein the protein is bovine G-CSF.

Other specific embodiments of the invention include a stabilized protein composition wherein the protein is bovine G-CSF and wherein the bG-CSF is present at a concentration in the range of 0.01 to 5 mg/ml.

Other specific embodiments of the invention include a stabilized protein composition wherein the protein is bovine G-CSF and wherein the stabilizing buffer is selected from the group consisting of: HEPES, TES and TRICINE.

Still other specific embodiments of the invention include a stabilized protein composition wherein the protein is bovine G-CSF and wherein the stabilizing buffer is present in a concentration ranging from about 0.05M to about 2M.

Still other specific embodiments of the invention include a stabilized protein composition wherein the protein is bovine G-CSF and wherein the composition is at a physiological pH.

Still other specific embodiments of the invention include a stabilized protein composition wherein the protein is bovine G-CSF and wherein the composition is at a physiological temperature.

Preferably, the stabilized protein composition of the invention is a composition comprising bovine G-CSF in HEPES buffer. More preferably, the HEPES buffer is in a concentration ranging from about 0.05M to about 2M. Such bovine G-CSF formulations are preferably at physiological pH, such as 7.5. Furthermore, such preferred bovine G-CSF formulations are capable of maintaining, for a sustained period, for from about at least 3 days to 7 days or more, therapeutic levels of bovine G-CSF.

Furthermore, the stabilized protein composition of the invention is a composition comprising bovine G-CSF in HEPES buffer which composition is capable of providing for an extended shelf life and storage. Preferably the HEPES buffer is in a concentration ranging from about 0.05M to about 2M. More preferably, such compositions contain are maintained at a pH of about 4.0 to about 7.5, preferably 4.0, and a temperature of less than about 40° C. and preferably about 4° C. The extended shelf life and storage is in the range of from about 3 weeks to about 18 months, and preferably, is in the range of from about 6 weeks to about 1 year.

The present invention further relates to a pharmaceutically acceptable dosage form of a stabilized protein composition for parenteral administration to a mammal, comprising a protein and a pharmaceutically acceptable stabilizing buffer, which composition is capable of maintaining therapeutic levels of such protein for a sustained period, wherein the protein is present in an amount sufficient to provide protection to a mammal for a sustained period of time.

Specific embodiments of the invention include a pharmaceutically acceptable dosage form wherein the dosage form further comprises a component selected from the group consisting of viscosity modifiers and surfactant.

The present invention further relates to a method of preparing a pharmaceutically acceptable dosage form of a stabilized protein composition for parenteral administration to a mammal, comprising the step of combining a protein and a stabilizing buffer, which stabilized protein composition is capable of maintaining therapeutic levels of such protein for a sustained period, wherein the protein is present in an amount sufficient to provide protection to a mammal for at least three days.

The present invention further relates to a method of treating or preventing infections in mammals comprising administering to the mammal a stabilized protein composition comprising administering to the mammal a therapeutically effective amount of a stabilized protein composition, wherein the stabilized protein composition comprises a protein and a stabilizing buffer, which composition is capable of maintaining therapeutic levels of such protein for a sustained period.

Specific embodiments of the invention include such a method of treating or preventing infections in mammals wherein the protein is G-CSF.

The present invention further relates to a method of treating or preventing mastitis, metritis or bovine respiratory disease in cattle, comprising administering to the mammal a stabilized G-CSF composition comprising administering to the mammal a therapeutically effective amount of a stabilized G-CSF composition, wherein the stabilized G-CSF composition comprises G-CSF and a stabilizing buffer, which composition is capable of maintaining therapeutic levels of such protein for a sustained period.

The present invention further relates to a method of maintaining therapeutic levels of a protein in a mammal for a sustained period, which comprises administering to the mammal a stabilized protein composition, wherein the stabilized protein composition comprises a protein and a stabilizing buffer, which composition is capable of maintaining therapeutic levels of such protein for a sustained period.

Specific embodiments of the invention include such a method of maintaining therapeutic levels of a protein in a mammal for a sustained period, wherein the stabilizing buffer is selected from the group consisting of HEPES, TES and TRICINE.

Other specific embodiments of the invention include such a method of maintaining therapeutic levels of a protein in a mammal for a sustained period, wherein the sustained period is at least about three days.

Other specific embodiments of the invention include such a method of maintaining therapeutic levels of a protein in a mammal for a sustained period, wherein the protein is selected from the group consisting of: colony stimulating factors, somatotropins, cytokines, antibodies and antigens. Specific examples of cytokines include interleukins, such as interleukins 1–18, and interferons, such as Interferons $\alpha$, $\beta$ and $\gamma$.

More specific embodiments of the invention include such a method of maintaining therapeutic levels of a protein in a mammal for a sustained period, wherein the protein is a colony stimulating factor.

Still other specific embodiments of the invention include such a method of maintaining therapeutic levels of a protein in a mammal for a sustained period, wherein the protein is selected from the group consisting of: human G-CSF, bovine G-CSF and canine G-CSF.

Still other specific embodiments of the invention include such a method of maintaining therapeutic levels of G-CSF in a mammal for a sustained period, wherein the G-CSF is present at a concentration in the range of 0.01 to 5 mg/ml.

Still other specific embodiments of the invention include such a method of maintaining therapeutic levels of G-CSF in a mammal for a sustained period, wherein the stabilizing buffer is selected from the group consisting of: HEPES, TES and TRICINE.

Still other specific embodiments of the invention include such a method of maintaining therapeutic levels of G-CSF in a mammal for a sustained period, wherein the stabilizing buffer is present in a concentration ranging from about 0.05M to about 2M.

Still other specific embodiments of the invention include such a method of maintaining therapeutic levels of G-CSF in a mammal for a sustained period, wherein the G-CSF is bovine G-CSF.

Still other specific embodiments of the invention include such a method of maintaining therapeutic levels of bG-CSF in a mammal for a sustained period, wherein the bG-CSF is present at a concentration in the range of 0.01 to 5 mg/ml.

Still other specific embodiments of the invention include such a method of maintaining therapeutic levels of bG-CSF in a mammal for a sustained period, wherein the stabilizing buffer is selected from the group consisting of: HEPES, TES and TRICINE.

Still other specific embodiments of the invention include such a method of maintaining therapeutic levels of bG-CSF in a mammal for a sustained period, wherein the stabilizing buffer is present in a concentration ranging from about 0.05M to about 2M.

The present invention further relates to a kit for administering to the mammal a stabilized protein composition comprising a first container having a therapeutically effective amount of a protein and a second container having a pharmaceutically acceptable stabilizing buffer, wherein the therapeutically effective amount of the protein of the first container when combined with the pharmaceutically acceptable stabilizing buffer of the second container, is capable of maintaining therapeutic levels of such protein in the mammal for a sustained period.

Specific embodiments of the invention include a kit of wherein the protein is present in an amount sufficient to provide protection to a mammal for at least three days.

A preferred composition of the invention is a stabilizing protein composition comprising bovine G-CSF and HEPES buffer, which composition is capable of maintaining therapeutic levels of bovine G-CSF in a mammal, in vivo, for at least 3 days, wherein the composition is at a pH of about 7.5 and wherein the composition is at a temperature of about physiological temperature or 40° C. Such a composition is particularly useful wherein the mammal is a cow. More particularly, the HEPES buffer is present at a concentration ranging from about 0.05M to about 2M. It is particularly preferable wherein the HEPES buffer is present at a concentration of about 1M. Preferably, the bovine G-CSF is present at a concentration in the range of about 0.01 to 5 mg/mL. Most preferably the concentration of bG-CSF is about 0.1 mg/mL.

Preferably, the invention further relates to a stabilized protein composition comprising bovine G-CSF and HEPES buffer, which composition is capable of providing for an extended shelf life in the range of from about 3 weeks to about 18 months. It is particularly preferred wherein the HEPES buffer is in a concentration ranging from about 0.05M to about 2M. It is also preferred wherein the composition is at a pH of about 7.5 and wherein the temperature of the composition is less than about 40° C., most preferably, about 4° C. It is also particularly preferred wherein the extended shelf life is in the range of from about 6 months to about 1 year. Alternatively, such stabilized composition capable of an extended shelf life can be maintained at a temperature of the composition of about 40° C.

DETAILED DESCRIPTION OF THE INVENTION

Figure 1:
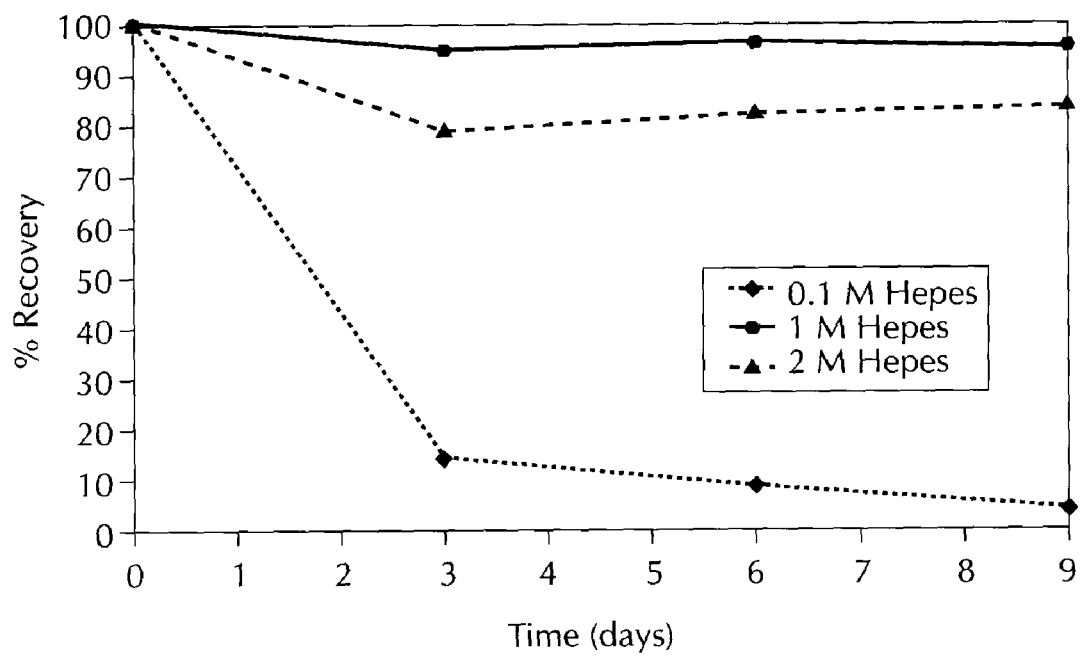
FIG. 1 shows the stability (% recovery) of 0.1 mg/ml bG-CSF solutions at pH 7.5, as a function of time, under storage conditions of 40° C. in concentrations of 0.1M, 1M and 2M HEPES buffer.

The present invention relates to stabilized protein compositions based on the surprising discovery that proteins, and in particular, proteins useful in treating infections in mammals, such as humans, dogs, cats, goats, sheep, horses and swine, can be stabilized by the addition of a stabilizing buffer, such as HEPES, TES and TRICINE to the protein such that the stabilized protein composition is capable of maintaining a sustained period of protein activity both in vivo and in vitro. With respect to in vivo activity, the stabilized protein compositions of the present invention can maintain therapeutically effective levels of such proteins in a mammal for a sustained period.

In particular, the present invention is a sustained release (sustained activity) formulation of bG-CSF in a stabilizing buffer, such as HEPES or TES, that provides a prolonged therapeutic drug activity. It is known that bG-CSF denatures at temperatures around 40° C. and is unstable at neutral pH. This is a concern since physiological pH is close to neutral and the body temperature of a cow is approximately 40° C.

The proteins of the stabilized compositions of the present invention can be naturally occurring proteins, isolated or purified proteins, or recombinantly produced proteins. Also included within the invention are all proteins which have been chemically modified chemical modification of proteins such as methionine oxidation, cysteine S-alkylation and disulfide addition with beta-mercaptoethanol, alkylation of lysine amino groups etc. A preferred protein for use in the stabilized protein compositions of the present invention is G-CSF, and most preferred is the protein bG-CSF.

By "G-CSF" is meant granulocyte colony stimulating factor, including granulocyte colony stimulating factor in its natural form as well as variants and mutants thereof, including, for example, recombinant variants having one or more amino acid deletions, substitutions and/or additions. Such variants and mutants retain all or sufficient biological activity to provide for a therapeutic benefit in a mammal. G-CSF in its natural form is a glycoprotein which comprises a protein having 174 amino acids, and a form having three additional amino acids. Both forms have five cysteine residues, four forming two disulfide bonds and one in free form.

Other examples of proteins suitable for use in the stabilized protein compositions of the present invention include, for example, activins, adhesion molecules, such as L-selectin, CD-18 and ICAM-1, chemokines, chemotactic factors, erythropoietin, growth factors, inhibins, insulin, interferons, such as α, β and γ; interleukins, such as interleukins 1–18, leptin, macrophage inflammatory proteins, macrophage migration inhibitory factor, macrophage stimulating protein, neurotrophins, neutrophil inhibitory factor, oncostatins, somatostatins, somatotrophins (all species), such as porcine, bovine or human, stem cell factors, tumor necrosis factors, thrombopoietins and cell associated and soluble receptors for all of the foregoing proteins and any and all other proteins which when administered to a mammal are capable of providing a beneficial or therapeutic result. Examples of particular proteins which can be used in the stabilized protein compositions of the present invention are shown in Table 1. Other proteins which can be used in the stabilized protein compositions of the present invention include those described in R&D Systems Catalogue, 614 McKinley Place NE, Minneapolis Minn. 55413, USA, incorporated herein by reference.

TABLE 1

Proteins of Potential Therapeutic Benefit $\beta_2$-Microglobulin ($\beta_2$-M)
6-Histidine
6Ckine
Amphiregulin (AR)
Angiogenin (ANG)
Annexin V TABLE 1-continued Proteins of Potential Therapeutic Benefit B-lymphocyte Cell Adhesion Molecule (BL-CAM)
beta Endothelial Cell Growth Factor (β-ECGF)
beta Nerve Growth Factor (β-NGF)
beta-Actin (β-Actin)
Betacellulin (BTC)
Brain-derived Neurotrophic Factor (BDNF)
CD31 (PECAM-1)
CDIO
Ciliary Neurotrophic Factor (CNTF)
Ciliary Neurotrophic Factor Receptor alpha (CNTF Rα)
CRG-2 (IP-10)
CXCR-1 (IL-8 RA)
CXCR-2 (IL-8 RB)
CXCR-3
CXCR-4 (Fusin)
Cytokine-induced Neutrophil Chemotactic Factor 1 (CINC-1])
Cytokine-induced Neutrophil Chemotactic Factor 2 beta (CINC-2β)
Cytokine-induced Neutrophil Chemototic Factor 2 alpha (CINC-2α)
Cytotoxic T-lymphocyte-associated Molecule 4 (CTLA-4)
E-Selectin
Endothelin-1 (ET-1)
Eotaxin (Eot)
Eotaxin-2 (Eot-2)
Epidermal Growth Facor (EGF)
Epithelial-derived Neutrophil Attractant 78 (ENA-78)
Erythropoietin Receptor (Epo R)
Erythropoietin (Epo)
Fas(CD95)
Fibroblast Growth Factor 4 (FGF4)
Fibroblast Growth Factor 5 (FGF-5)
Fibroblast Growth Factor 6 (FGF-6)
Fibroblast Growth Factor 7/KGF (FGF-7)
Fibroblast Growth Factor 8 (FGF-8)
Fibroblast Growth Factor 8b (FGF-8b)
Fibroblast Growth Factor 8C (FGF-8c)
Fibroblast Growth Factor 9 (FGF-9)
Fibroblast Growth Factor acidic (FGF acidic)
Fibroblast Growth Factor basic (FGF basic)
Fibronectin (FN)
Fit-1
Fit-3 Ligand
Fractalkine
Glial Cell Line-derived Neurotropic Factor (GDNF)
Glycoprotein 130 (gp 130)
Granulocyte Chemotactic Protein (GCP-2)
Granulocyte Colony Stimulating Factor (G-CSF)
Granulocyte Colony Stimulating Factor Receptor (G-CSF R)
Granulocyte Macrophage Colony Stimulating Factor (GM-CSF)
Growth Related Protein (GRO)
Growth Related Protein alpha (GROα)
Growth Related Protein beta (GROβ)
Growth Related Protein gamma (GROγ)
Hemofiltrate CC Chemokine I (HCC-1)
Heparin Binding Epidermal Growth Factor (HB-EGF)
Hepatocyte Growth Factor (HGF)
Heregulin alpha (HRG-α)
Heregulin beta 1 (HRG-β1)
I-309
Insulin-like Growth Factor (IGF-1)
Interferon gamma (IFN.γ)
Interleukin 1 receptor antagonist (IL-1ra)
Interleukin 11 Receptor (IL-11R)
Interleukin 12 p7O (IL-12 p7O)
Interleukin 13 (IL-13)
Interleukin 16 (IL-16)
Interleukin 2 Receptor alpha (IL-2 Rα)
Interleukin 2 Receptor beta (IL-2 Rβ)
Interleukin 3 (IL-3)
Interleukin 4 Receptor (IL-4 R)
Interleukin 5 (IL-5)
Interleukin 7 Receptor (IL-7 R)
Interleukin 9 (IL-9)
IP-10
JE/MCP-I
Keratinocyte Growth Factor/FGF-7 (KGF)
L-Selectin TABLE 1-continued Proteins of Potential Therapeutic Benefit Latency-associated Peptide (TGF-β1) (LAP TGF-β1)
Latent Transforming Growth Factor beta 1 (Latent TGF-β1)
Lepfln (0B)
Leptin Receptor (Leptin R)
Leukemia Inhibitory Factor Receptor alpha (LIF Rα)
Leukemia Inhibitory Factor (LIF)
LFA-1
Insulin-like Growth Factor I Receptor (IGF-I R)
Insulin-like Growth Factor II (IGF-II)
Intercellular Adhesion Molecule 3 (ICAM-3)
Intercellular Adhesion Molecule I (ICAM-1)
Intereukin 11 (IL-11)
Interleukin 1 Receptor type I (IL-1 RI)
Interleukin 10 (IL-10)
Interleukin 10 Receptor (IL-10 R)
Interleukin 12 (IL-12)
Interleukin 12 p4O (IL-12 p4O)
Interleukin 13 Receptor alpha (IL-13 Rα)
Interleukin 15 (IL-15)
Interleukin 17 (IL-17)
Interleukin 18/1G1F (IL-18)
Interleukin 2 (IL-2)
Interleukin 2 Receptor gamma (IL-2 Rγ)
Interleukin 3 Receptor alpha (IL-3 Rα)
Interleukin 4 (IL-4)
Interleukin 5 Receptor alpha (IL-5 Rα)
Interleukin 6 (IL-6)
Interleukin 6 Receptor (IL-6 R)
Interleukin 7 (IL-7)
Interleukin 8 (IL-8)
Interleukin 9 Receptor (IL-9 R)
Interleukin I alpha (IL-Iα)
Interleukin I beta (IL-Iβ)
Interleukin I Receptor type II (IL-1 RII)
Mac-1 alpha chain
Macrophage Colony Stimulating Factor (M-CSF)-
Macrophage Colony Stimulating Factor Receptor (M-CSF R)
Macrophage Inflammatory Protein 1 gamma (MIP-1γ)
Macrophage Inflammatory Protein 2 (MIP-2)
Macrophage Inflammatory Protein 3 alpha (MIP-3α)
Macrophage Inflammatory Protein 3 beta (MIP-3β)
Macrophage Inflammatory Protein I alpha (MIP-1α)
Macrophage Inflammatory Protein I beta (MIP-1β)
Macrophage Migration Inhibitory Factor (MIF)
Macrophage Stimulating Protein (MSP)
Macrophage-derived Chemokine (MDC/DC-CK1)
MARC/MCP-3
Midkine (MK)
MIG
Monocyte Chemotaclic Protein 1/MCAF (MCP-1)
Monocyte Chemotactic Protein 2 (MCP-2)
Monocyte Chemotactic Protein 3 (MCP-3)
Monocyte Chemotactic Protein 4 (MCP-4)
Monocyte Chemotactic Protein 5 (MCP-5)
Neural Cell Adhesion Molecule (NCAM))
Neurotrophin 3 (NT-3)
Neurotrophin 4 (NT-4)
of Potential Therapeutic Benefit
Oncostatin M (OSM)
P-Selectin (CD62P)
Placenta Growth Factor (PIGF)
Placenta Growth factor 2 (PIGF-2)
Plasma Selenium Glutathione Peroxidases.
Platelet GPIIb/GPIIIa (CD41a)
Platelet-derived Endothelial Cell Growth Factor (PD-ECGF)
Platelet-derived Growth Factor (PDGF)
Platelet-derived Growth Factor A Chain (PDGF A Chain)
Platelet-derived Growth Factor AA (PDGF-AA)
Platelet-derived Growth Factor AB (PDGF-AB)
Platelet-derived Growth Factor B Chain (PDGF B Chain)
Platelet-derived Growth Factor BB (PBGF-BB)
Platelet-derived Growth Factor Receptor alpha (PDGF Rα)
Platelet-derived Growth Factor Receptor beta (PDGF Rβ)
Pleiotrophin (PTN)
Pre-B Cell Growth Stimulating Factor/SDF-1 (PBSF)
RANTES
Secretory Leukocyte Protease Inhibitor (SLPI)

TABLE 1-continued

Proteins of Potential Therapeutic Benefit

Stem Cell Factor Receptor (SCF R)
Stem Cell Factor (SCF)
Stromal Cell-derived Factor 1 beta/PBSF (SDF-Iβ)
Stromal Cell-derived Factor 1/PBSF (SDF-1)
Stromal Cell-derived Factor I alpha/PBSF (SDF-Iα)
Thrombopoietin (Tpo)
Thymus and Activation-regulated Chemokine (TARC)
Thymus-expressed Chemokine (TECK)
Transforming Growth Factor alpha (TGF-α)
Transforming Growth Factor beta (TGF-β)
Transforming Growth Factor beta 1.2 (TGF-β1.2)
Transforming Growth Factor beta 2 (TGF-β2)
Transforming Growth Factor beta Binding Protein I (TGF-β bpl)
Transforming Growth Factor beta I (TGF-β1)
Transforming Growth Factor beta Receptor type II (TGF-β RII)
Transforming Growth Factor beta Receptor type III (TGF-β RIII)
Transforming Growth Factor/Beta 5 (YGF-β5)
Trasforming Growth Factor beta 3 (TGF-β3)
TrkB
Tumor Necrosis Factor alpha (TNF-α)
Tumor Necrosis Factor beta (TNF-β)
Tumor Necrosis Factor Receptor type I (TNF RI)
Tumor Necrosis Factor Receptor type II (TNF RII)
Vascular Cell Adhesion Molecule 1 (VCAM-1)
Vascular Endothelial Growth Factor (VEGF)

Preferred proteins are those which are useful in treating or preventing infections in mammals, such as humans, dogs, cattles, swine, goats, sheep, horses and cats. Such infections may be bacterial infections or protozoal infections, or may be caused by viruses.

As used herein, unless otherwise indicated, the term "infection(s)" includes bacterial protozoa, fungal and viral infections that occur in mammals, as well as disorders related to such infections that may be treated or prevented by administering the stabilized protein compositions the present invention.

Infectious diseases which may be treated using the stabilized protein compositions of the present invention include, but are not limited to infectious diseases of cattle, such as, for example, bovine mastitis, associated with but not limited to *Staphylococcus aureus, Escherichia coli, Streptococcus uberis, Streptococcus dysgalactia, Streptococcus, agalactiae, Klebsiella* sp. *Corynebacterium* sp bovine respiratory disease, associated with but not limited to infectious bovine rhinotracheitis virus (IBR), parainfluenza virus (P13), bovine viral diarrhea virus (BVD), *Pasteurella haemolytica, Pasteurella multocida* and *Haemophilus somnus*; reproductive diseases such as metritis; and bovine diarrhea associated with but not limited to *E. coli* and *Eimeria* sp.

Other examples of infectious diseases which may be treated using the stabilized protein compositions of the present invention include, but are not limited to infectious diseases of dogs such as pyoderma, and respiratory disease in dogs, also referred to as kennel cough.

The stabilized protein composition of the present invention can be used for providing therapeutic benefits other than in treating or preventing infections. One example of a therapeutic benefit or effect other than in treating or preventing infections is the administration of recombinant human G-CSF to dogs and cats to ameliorate chemotherapy induced myelosuppression and to allow for more aggressive cancer treatment protocols.

As used herein, the word "stabilizing", except as otherwise indicated, refers to maintained therapeutic levels of the protein, for a sustained period of time. Such maintained therapeutic levels of the protein can occur, either after administration to a mammal, or in vitro, prior to use or during storage of the stabilized protein composition of the invention. The stability of the protein compositions of the invention can be determined, for example, by the % initial concentration versus time, using the methods described herein.

After administration to a mammal, the stabilized compositions of the present invention provides for maintained therapeutic levels of the protein, such that the protein is capable of providing its therapeutic or beneficial effect over a sustained period. As used herein, and unless otherwise indicated, the term "sustained period" refers to that period of time in which therapeutic levels of the protein are maintained, either after administration to a mammal, or, alternatively, in vitro, prior to use, or during storage of the stabilized protein composition of the invention.

A sustained period of protein therapeutic levels provides for a beneficial or therapeutic effect in the mammal for a longer period of time than that which is possible by administration of the same protein to the mammal without the presence of the stabilizing buffer, as compared with, for example, a control solution of the protein in water or PBS. Alternatively, under conditions of in vitro storage, the sustained period of protein therapeutic levels provides for increased stability of the protein for a longer period of time than that which is possible by storage of the same protein under conditions without the presence of the stabilizing buffer, such as when compared with for example, a control solution of the protein in water or PBS. Preferably, the sustained period is at least three days. Most preferably, the sustained period is around seven days or greater.

As used herein, and unless otherwise indicated, the term "therapeutic levels" refers to that amount of a protein which provides therapeutic effect in various administration regimens. Such amounts are readily determined by those skilled in the art. The amount of protein will depend on the type and severity of the infection, the route of administration, etc.

By "stabilizing buffer" is meant any of several buffers which, when combined with the protein of the stabilized composition of the present invention, provide for a stabilized protein composition, which composition is capable of maintaining therapeutic levels of such protein for a sustained period. Maintenance of therapeutic levels can be determined, for example, by measuring protein activity, as determined by methods known in the art. Preferably, the stabilizing buffer operates at physiological pH. Stabilizing buffers include, but are not limited to, organic buffers, such as those zwitterionic buffers, generally referred to as "Good buffers" which operate within the range of 6 to 8.5. Examples of such stabilizing buffers include: HEPES (N-2-Hydroxyethylpiperazine-N-2-ethanesulfonic acid), TES (N-Tris(hydroxymethyl) methyl-2 aminoethanesulfonic acid), and TRICINE (N-Tris(hydroxymethyl)methylglycine), cacodylic acid, Bis(2-hydroxyethyl)-imino-tris(hydroxymethyl)methane (BISTRIS), Piperazine N,N'bis-(2 ethane sulfonic acid) (PIPES), Imidazole and Tris(hydroxymethyl)aminomethane (TRIS). Examples of buffers which can be used in the stabilized protein compositions of the present invention are shown in Table 2.

TABLE 2

| Buffer | | $pK_a$ |
|---|---|---|
| MES | 2-(N-morpholino)ethane sulfonic acid | 5.96 |
| bis-tris | bis-(2-hydroxyethyl)imino-tris-(hydroxymethyl)methane | 6.36 |

TABLE 2-continued

| Buffer | | $pK_a$ |
|---|---|---|
| ADA | N-2-acetamidoiminodiacetic acid | 6.43 |
| ACES | N-(2-acetamido)iminodiacetic acid | 6.54 |
| PIPS | piperazine-N,N'-bis(2-ethanesulfonic acid) | 6.66 |
| MOPSO | 3-(N-morpholine)-2-hydroxypropane sulfonic acid | 6.75 |
| bis-tris propane | 1,3-bis[tris(hydroxymethyl)methylamino]propane | 6.80 |
| BES | N,N-bis-(2-hydroxyethyl)-2-aminoethane sulfonic acid | 6.88 |
| MOPS | 3-(N-morpholine)propane sulfonic acid | 7.01 |
| TES | N-tris-(hydroxymethyl)methyl-2-aminoethane sulfonic acid | 7.16 |
| HEPES | N-2-hydroxyethylpiperazine-N'-2-aminoethane sulfonic acid | 7.31 |
| DIPSO | 3-[N-bis(hydroxyethyl)-amino]-2-hydroxypropane sulfonic acid | 7.35 |
| TAPSO | 3-[N-(tris-hydroxymethyl)methylamino]-2-hydroxypropane sulfonic acid | 7.39 |
| POPSO | pierazine-N,N'bis-(2-hydroxypropane sulfonic acid) | 7.63 |
| HEPPSO | N-hydroxyethylpiperazine-N'-2-hydroxypropane sulfonic acid | 7.73 |
| Tricine | N-tris(hydroxymethyl)methylglycine | 7.79 |
| EPPS | N-2-hydroxyethylpiperazine-N'-2-aminopropane sulfonic acid | 8.00 |
| bicine | N,N-bis-(2-hydroxyethyl)glycine | 8.04 |
| TAPS | N-tris(hydroxymethyl)methyl-3-aminopropane sulfonic acid | 8.11 |
| AMPSO | 3-N-($\alpha,\alpha$-dimethylhydroxuethyl)-amino-2-hydroxypropane sulfonic acid | 9.10 |
| CAPSO | 3-N-cyclohexylamino sulfonic acid | 9.43 |

The pH of the stabilized protein composition of the present invention can be in the range of from about 4.0 to about 8.

As used herein, the term "physiological pH", except as otherwise indicated, refers to the range in pH found in mammals, including (humans, cattle, swine, horses, goats, sheep, dogs and cats. The physiological pH of mammals is generally within the range of from about 6.5 to about 8.0.

The temperature of the stabilized protein composition of the present invention can be in the range of from about 20° C. to about 50° C.

As used herein, the term "physiological temperature", except as otherwise indicated, refers to the range in body temperatures found in mammals, including humans, cattle, swine, horses, goats, sheep, dogs and cats. The physiological temperature of mammals is generally within the range of from about 37° C. to about 41° C. The physiological temperatures for some exemplary mammals are as follows: humans, 37° C.; cattle, 39° C.; cats, 38° C.; dogs, 39° C.; goats, 39° C.; horses, 37° C.; and pigs, 37° C.

Preferably, the stabilized protein compositions of the present invention contain as the protein, G-CSF, and more preferably, bovine G-CSF, in a stabilizing buffer, which buffer is selected from HEPES buffer, TES buffer and TRICINE buffer. The resulting stabilized protein composition is capable of maintaining the activity of bG-CSF at therapeutically effective levels for a sustained period of at least three days, at the physiological pH of cattle and at the physiological temperature for cattle of about 40° C.

A stabilized protein composition can be prepared by combining the protein and stabilizing buffer using known and generally available combining techniques. A particular method for preparing a stabilized protein composition includes using the protein in a purified form, prepared in accordance with protein purification techniques known to those skilled in the art.

For a particular protein of therapeutic value, one can dissolve the particular protein (up to its maximum solubility) in each of several buffers, such as HEPES, TES, TRICINE or other buffers, at varying buffer concentrations, such as from 0.05 to 2M. Further, the pH of the solution can be varied, typically from about pH 4.0 to about 8.0. The maximum solubility of the protein in a particular buffer can be determined by conventional means known in the art. The solution can then be stored at the physiological temperature of a mammal that the protein solution is intended to be administered to, and the amount of protein present in the solution can be determined as a function of time. The therapeutic level of protein in the solution can be determined by monitoring the % recovery of protein as a function of time. The amount of protein remaining or % recovery of protein can be compared to a known threshold level of protein required for therapeutic benefit. The sustained period of time can then be determined as the number of days during which the amount of protein remaining in the solution is equal to or greater than the known threshold level of protein required for therapeutic benefit. A buffer which is effective as a stabilizing buffer is one which, when combined with the particular protein, will provide for maintained therapeutic levels of the protein for a sustained period, that is, a period of time longer than that which is possible by administration of the same protein to the mammal without the presence of the stabilizing buffer.

The stability of a protein can be determined by measuring the activity of the protein as a function of time. The unfolding temperature ($T_m$) of the protein can be used as a marker of solution stability and in vivo stability for proteins. The unfolding temperature of a particular protein refers to that temperature at which the protein loses its secondary structure and typically, its activity and can be determined using methods known to those of skill in the art, such as differential scanning calorimetry.

The amounts of protein present in the stabilized protein compositions of the present invention can range from about 0.1 mg/ml to about 5 mg/ml. For G-CSF the preferred range is from about 0.1 mg/ml to about 3 mg/ml.

One example of a stabilized protein composition in accordance with the present invention is a composition containing bG-CSF and HEPES buffer wherein the bG-CSF is present in a concentration range of from about 0.1 to about 5 mg/ml and wherein the HEPES buffer is present in a concentration range of from about 0.1M to about 2M. More preferably the bG-CSF concentration is within the range of from about 0.1 mg/ml to about 3 mg/ml.

Another example of a stabilized protein composition in accordance with the present invention is a composition containing bG-CSF and TES buffer wherein the bG-CSF is present in a concentration range of from about 0.1 to about 5 mg/ml and wherein the HEPES buffer is present in a concentration range of from about 0.1M to about 2M. More preferably the bG-CSF concentration is within the range of from about 0.1 mg/ml to about 3 mg/ml.

Yet another example of a stabilized protein composition in accordance with the present invention is a composition containing bG-CSF and TRICINE buffer wherein the bG-CSF is present in a concentration range of from about 0.1 to about 5 mg/ml and wherein the HEPES buffer is present in a concentration range of from about 0.1M to about 2M. More preferably the bG-CSF concentration is within the range of from about 0.1 mg/ml to about 3 mg/ml.

The stabilized protein composition of the present invention can be prepared in a frozen form or a lyophilized form using conventional means known to those of skill in the art. Lyophilized forms of the protein can be reconstituted with the stabilizing buffer. The solution can, alternatively, be stored in liquid form for immediate use. Preferably, the stabilized protein composition of the present invention is in a liquid form which maintains its activity in long term storage.

The stabilized protein compositions of the present invention can be administered orally, parenterally (subcutaneously, intravascularly, intraperitoneally and intramuscularly) nasally, such as by inhalation, intraocularly or intradermally or by infusion methods using forms known to those of skill in the art. Parenteral administration is preferred.

Regardless of the route of administration, the stabilized protein compositions of the present invention can be formulated into pharmaceutically acceptable dosage forms by conventional methods known or apparent to those of skill in the art.

The pharmaceutically acceptable dosage forms of the stabilized protein compositions of the present invention are preferably, suitable for subcutaneous admininstration. A pharmaceutically acceptable dosage form for subcutaneous administration is typically, of a volume not greater than about 20 ml (such as for admininstration to horses and cattle), is sterile (suitable for use in mammals), and further, is well-tolerated by the mammal, that is, does not induce appreciable swelling, pain or necrosis at the injection site.

In general, the pharmaceutically acceptable dosage forms of the present invention may contain other pharmaceutically acceptable components, such as, for example, surfactants or detergents, viscosity modifying agents, sugars, or proteins, which additional components are present in amounts suitable for effective, safe pharmaceutical administration. For example, the pharmaceutically acceptable dosage form of the stabilized protein compositions of the present invention can be formulated following accepted convention using carriers, stabilizers, diluents and/or preservatives. Diluents can include water, saline, dextrose, ethanol, glycerol, and the like. Additives for isotonicity can include sodium chloride, dextrose, mannitol, sorbitol, and lactose, among others. Stabilizers can include albumin, among others. Suitable other vehicles and additives are known, or will be apparent, to those skilled in the art.

The stabilized protein composition of the present invention can be provided in a kit, comprising a first container having a therapeutically effective amount of a protein and a second container having a pharmaceutically acceptable stabilizing buffer. The protein can be in a solid, such as frozen or lyophilized form, or in a liquid form. The stabilizing buffer can then be combined with the protein and administered to a mammal, such that the therapeutically effective amount of the protein of the first container when combined with the pharmaceutically acceptable stabilizing buffer of the second container, is capable of maintaining therapeutic levels of such protein in the mammal for a sustained period.

Specific embodiments of the invention include a kit of wherein the protein is present in an amount sufficient to provide protection to a mammal for at least three days. The pharmaceutically acceptable dosage form of the present invention can be in the range of from about 0.1 $\mu$g/kg to about 50 $\mu$g/kg, preferably from about 1 $\mu$g/kg to about 25

μg/kg and most preferably from about 3 μg/kg to about 25 μg/kg. The most preferred dosage form is about 24 μg/kg for use with b-G-CSF. The dose is effective for at least about three days.

The Examples provided below illustrate specific embodiments of the invention, but the invention is not limited in scope to the Examples specifically exemplified.

EXAMPLE 1

Sustained Stability of bG-CSF In HEPES, TES and TRICINE Buffers

Buffer concentrations of 0.1M, 1M and 2 M were prepared for each of three buffers, HEPES (N-2-Hydroxyethylpiperazine-N-2-ethanesulfonic acid), TES (N-Tris(hydroxymethyl) methyl-2 aminoethanesulfonic acid), and TRICINE (N-Tris(hydroxymethyl)methylglycine). Buffers were obtained from Fluka Biochemica USA. The pH of each buffer was adjusted to 7.5 using sodium hydroxide (J.T. Baker, USA). The buffers were sterile filtered using a 0.2 micron GV filter (Millipore USA). The buffers concentrations which were prepared were HEPES buffer: 0.1M, 1M and 2M; TES buffer: 0.1M, 1M and 2M; TRICINE buffer: 0.1M, 1M and 2M.

Solutions containing 0.1 mg/ml bG-CSF were prepared in each of the buffers, TES, TRICINE and HEPES in each of the buffer concentrations noted above, by adding an amount of 4.69 mg of bulk bG-CSF (based on a potency of 53.3%) to a 25 ml volumetric flask, which was then brought to volume with the appropriate buffer concentration.

Solutions containing 2 mg/ml bG-CSF were prepared in each of the buffers, TES, TRICINE and HEPES in each of the buffer concentrations noted in Table 1 by adding an amount of 93.8 mg of bulk bG-CSF (based on a potency of 53.3%) to a 25 ml volumetric flask, which was then brought to volume with the appropriate buffer concentration.

The bG-CSF formulations were then filtered through a 0.22 micron low protein binding filter (Millipore G. V.). A volume of 1 ml of each formulation was placed in a 1 ml vial and then placed in an oven at 40° C. oven for 9 days. The bG-CSF buffer stabilized solutions which were prepared were 0.1 mg/ml bG-CSF in (1) HEPES buffer: 0.1M, 1M and 2M; (2) TES buffer: 0.1M, 1M and 2M; and (3) TRICINE buffer: 0.1M, 1M and 2M. Samples removed from each of the vials every three days and analyzed by size exclusion HPLC (SEC-HPLC). The results are shown in FIGS. 1 to 6 and Tables 3 and 4.

TABLE 3

| Time | HEPES | | | TES | | | TRICINE | | |
|---|---|---|---|---|---|---|---|---|---|
| (days) | 0.1M | 1M | 2M | 0.1M | 1M | 2M | 0.1M | 1M | 2M |
| 0 | 100% | 100% | 100% | 100% | 100% | 100% | 100% | 100% | 100% |
| 3 | 15% | 95% | 78% | 16% | 85% | 100% | 17% | 85% | 94% |
| 6 | 9% | 96% | 82% | 11% | 97% | 98% | 10% | 79% | 88% |
| 9 | 5% | 95% | 83% | 9% | 93% | 98% | 5% | 70% | 86% |

Table 3 shows the % recovery (remaining) of 0.1 mg/ml bG-CSF solutions, prepared as described above, as a function of time. The solutions were stored at 40° C.

TABLE 4

| Time | HEPES | | | TES | | | TRICINE | | |
|---|---|---|---|---|---|---|---|---|---|
| (days) | 0.1M | 1M | 2M | 0.1M | 1M | 2M | 0.1M | 1M | 2M |
| 0 | 100% | 100% | 100% | 100% | 100% | 100% | 100% | 100% | 100% |
| 3 | 2% | 43% | 62% | 3% | 78% | 95% | 2% | 46% | 72% |
| 6 | 0% | 37% | 54% | 2% | 75% | 89% | 0% | 38% | 65% |
| 9 | 0% | 33% | 49% | 0% | 70% | 88% | 0% | 31% | 58% |

Table 4 shows the % recovery (remaining) of 2.0 mg/ml bG-CSF solutions, prepared as described above, as a function of time. The solutions were stored at 40° C.

Figure 2:
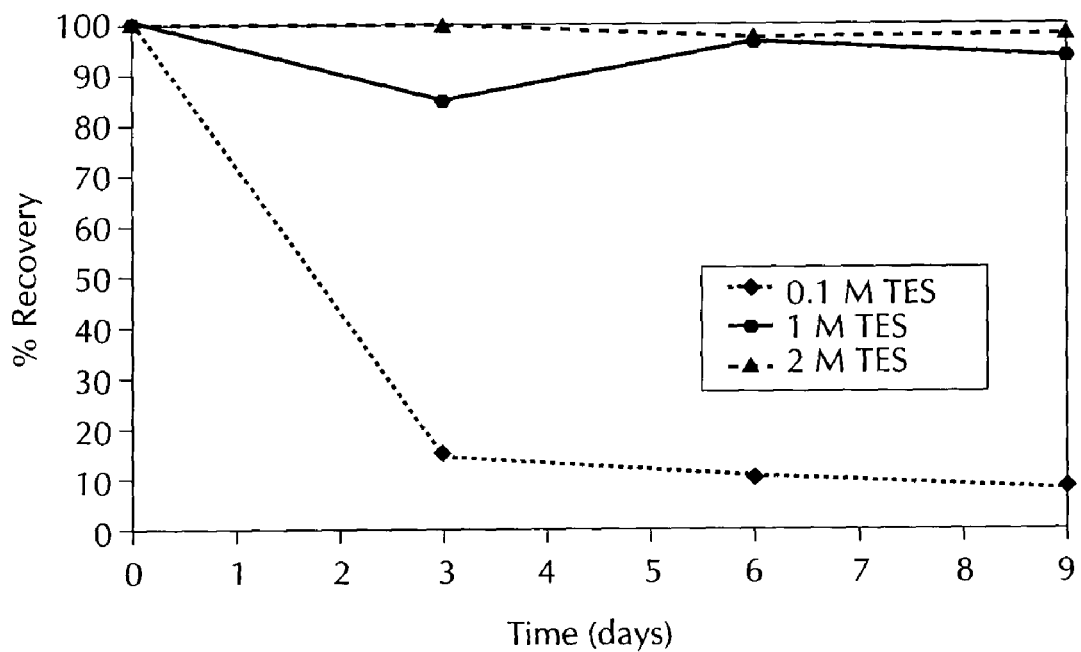
FIG. 2 shows the stability (% recovery) of 0.1 mg/ml bG-CSF solutions at pH 7.5, as a function of time, under storage conditions of 40° C. in concentrations of 0.1M, 1M and 2M TES buffer.
Figure 3:
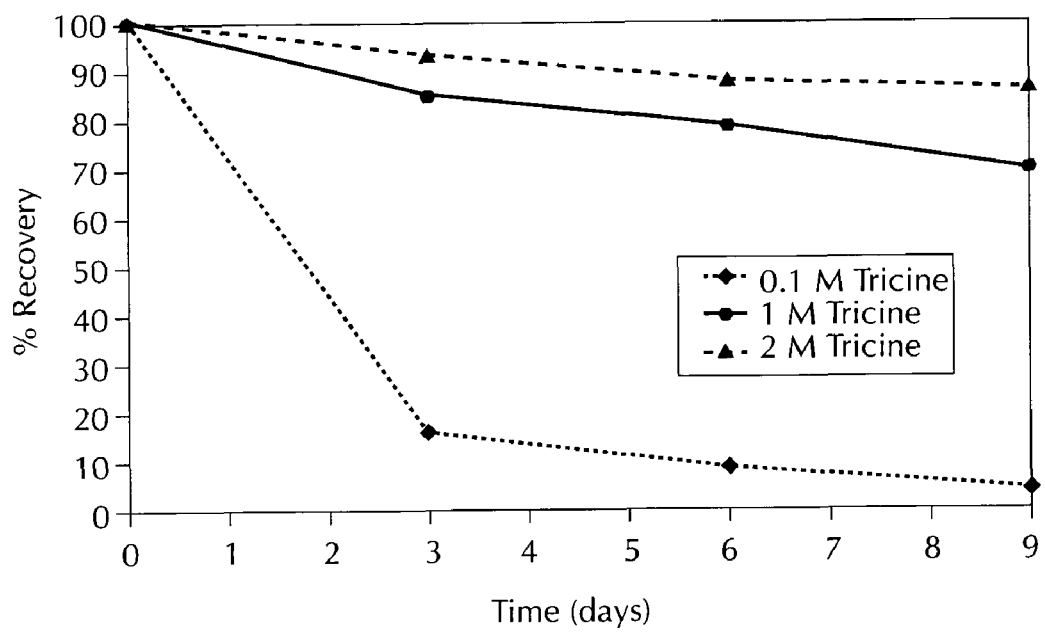
FIG. 3 shows the stability (% recovery) of 0.1 mg/ml bG-CSF solutions at pH 7.5, as a function of time, under storage conditions of 400 C in concentrations of 0.1M, 1M and 2M TRICINE buffer.

FIGS. 1 to 3 show the stability of 0.1 mg/ml bG-CSF solutions at pH 7.5, under storage conditions of 40° C. in varying concentrations of 0.1M, 1M and 2M HEPES, TES, and TRICINE buffers, respectively. The stability or maintenance of bG-CSF activity improved as the buffer concentration was increased to 1M and above, as shown in FIGS. 1 to 3. At 0.1 mg/ml bG-CSF there was 90% recovery of bG-CSF in 1M HEPES (FIG. 1).

Figure 4:
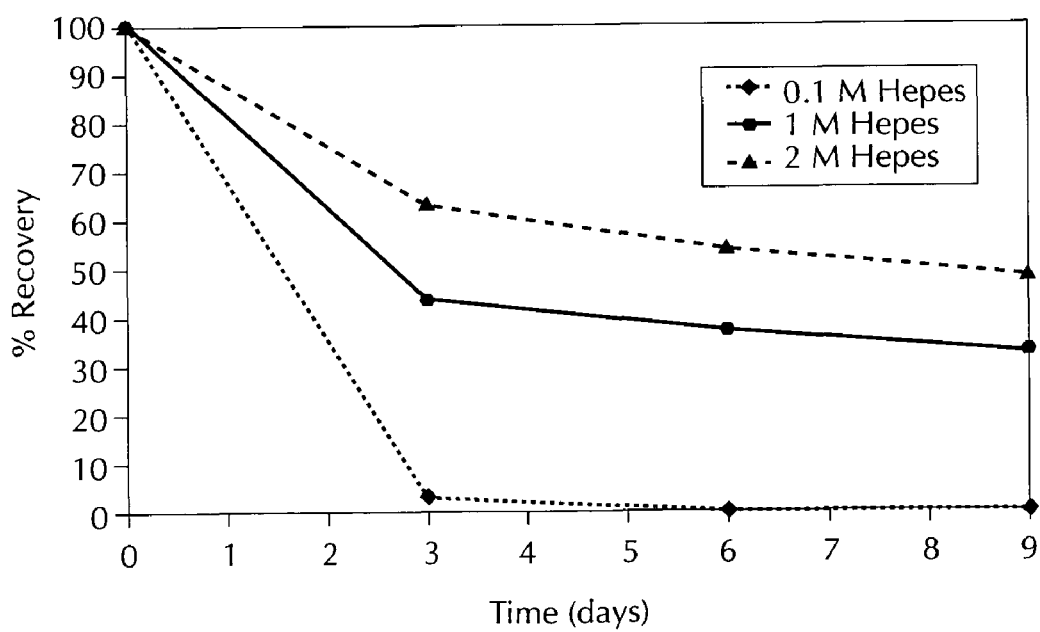
FIG. 4 shows the stability (% recovery) of 2 mg/ml bG-CSF solutions at pH 7.5, as a function of time, under storage conditions of 400 C in concentrations of 0.1M, 1M and 2M HEPES buffer.
Figure 5:
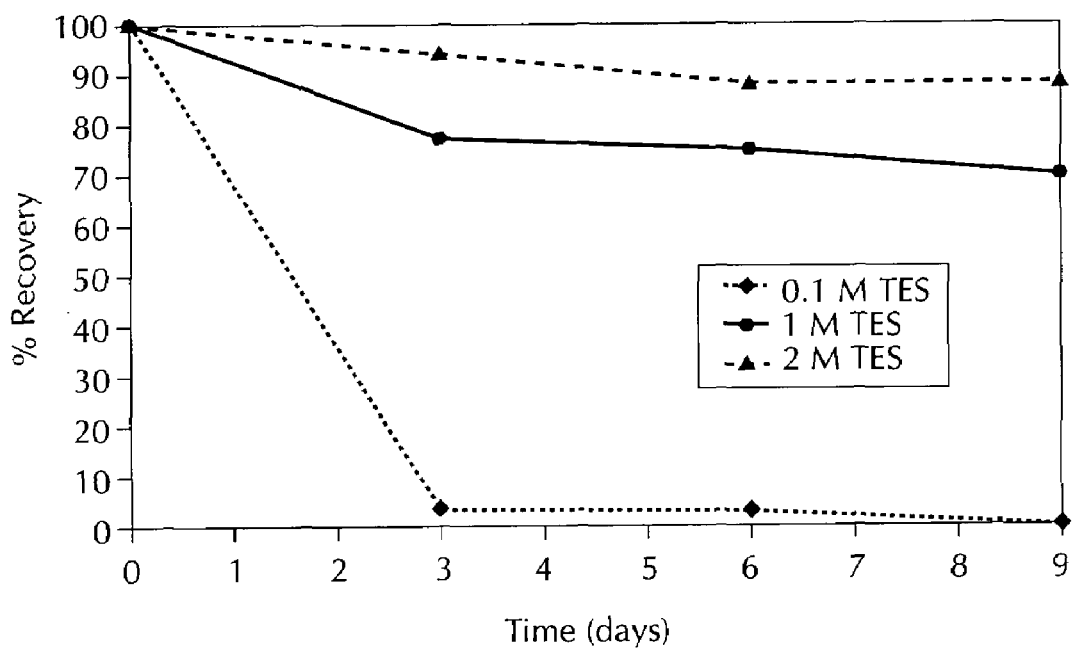
FIG. 5 shows the stability (% recovery) of 2 mg/ml bG-CSF solutions at pH 7.5, as a function of time, under storage conditions of 40° C. in concentrations of 0.1M, 1M and 2M TES buffer.
Figure 6:
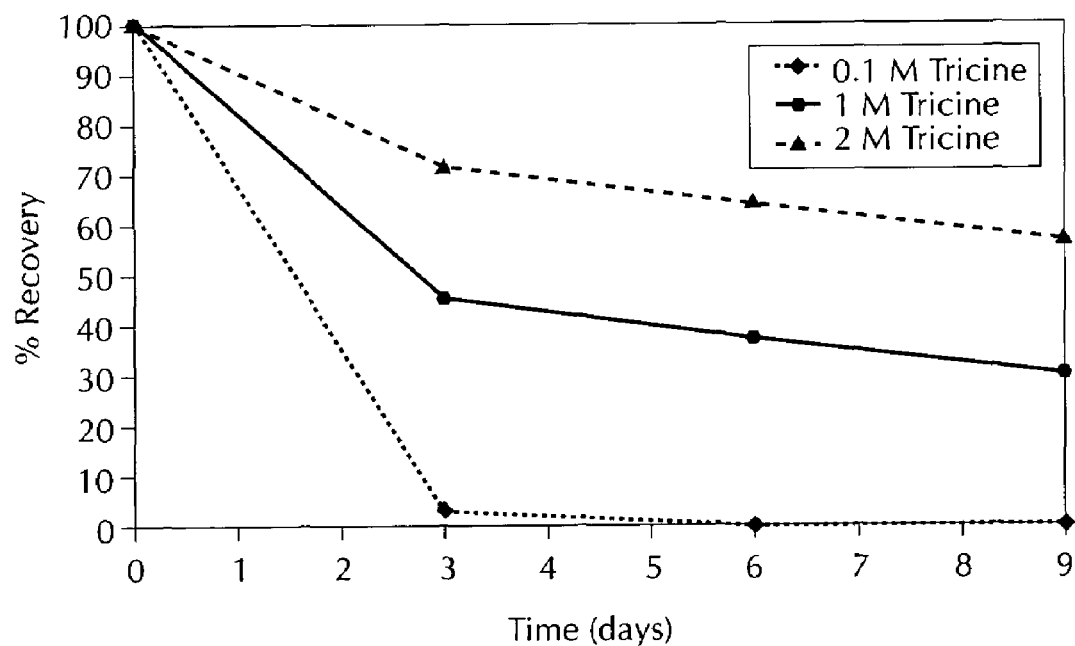
FIG. 6 shows the stability (% recovery) of 2 mg/ml bG-CSF solutions at pH 7.5, as a function of time, under storage conditions of 40° C. in concentrations of 0.1M, 1M and 2M TRICINE buffer.

FIGS. 4 to 6 show the stability of 2.0 mg/ml bG-CSF solutions at pH 7.5, under storage conditions of 40° C. in varying concentrations of 0.1M, 1M and 2M HEPES, TES, and TRICINE buffers, respectively. Again, the stability or maintenance of bG-CSF activity improved as the buffer concentration was increased to 1M and above, as shown in FIGS. 4 to 6.

The data presented in Tables 3 and 4 and FIGS. 1 to 6 show that the presence of buffers, HEPES, TES and TRICINE significantly maintain the activity of bG-CSF for sustained periods, from 3 to 9 days.

EXAMPLE 2

In Vivo Performance of bG-CSF Formulated in Water, 1M HEPES, 1M TES and 1M TRICINE Buffers In vivo testing of bG-CSF formulated in water, 1M HEPES, 1M TES and 1M TRICINE Buffers was performed in calves. A 24 μg/kg dose was administered to calves and the PMN (neutrophil) numbers monitored.

Figure 7:
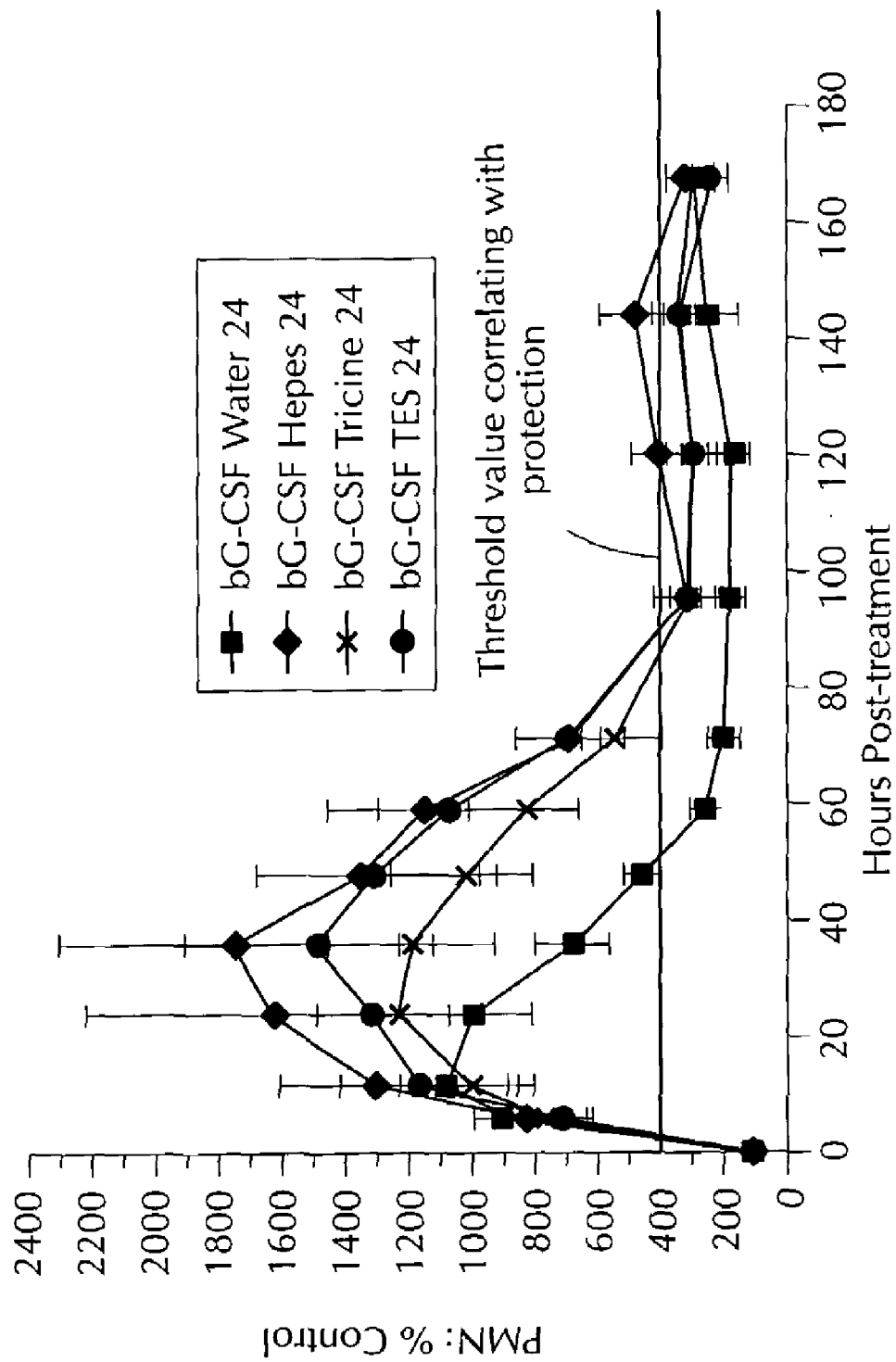
FIG. 7 shows total peripheral blood PMN counts (expressed as percent control, 0 hour value) for cattle treated with bG-CSF formulated in water, 1M HEPES buffer, 1M TES buffer and 1M TRICINE buffers.

FIG. 7 shows the total peripheral blood PMN counts (expressed as percent control, 0 hour value) for cattle treated with bG-CSF formulated in water, 1M HEPES buffer, 1M TES buffer and 1M TRICINE buffer. All three buffers gave approximately 100 hours of coverage from a single injection. This demonstrates that all three buffers provide for a sustained period of protein activity in vivo at the injection site.

EXAMPLE 3

Effect of HEPES Buffer on In Vitro Stability of bG-CSF

Amounts of bG-CSF were formulated in various buffer systems, as described below, at a concentration of 0.1 mg/ml in a pH range of about 7.0 to about 8.5. All samples were filtered with a 0.2 micron filter (GV Millipore, USA) prior to full. The samples were set up on stability at 40° C. and were monitored for 7 to 10 days by reverse phase HPLC (RP HPLC), SEC HPLC and bio-assay, as described below. The unfolding temperature of bG-CSF was measured by a VP-DSC MicroCalorimetry system (USA).

Figure 8:
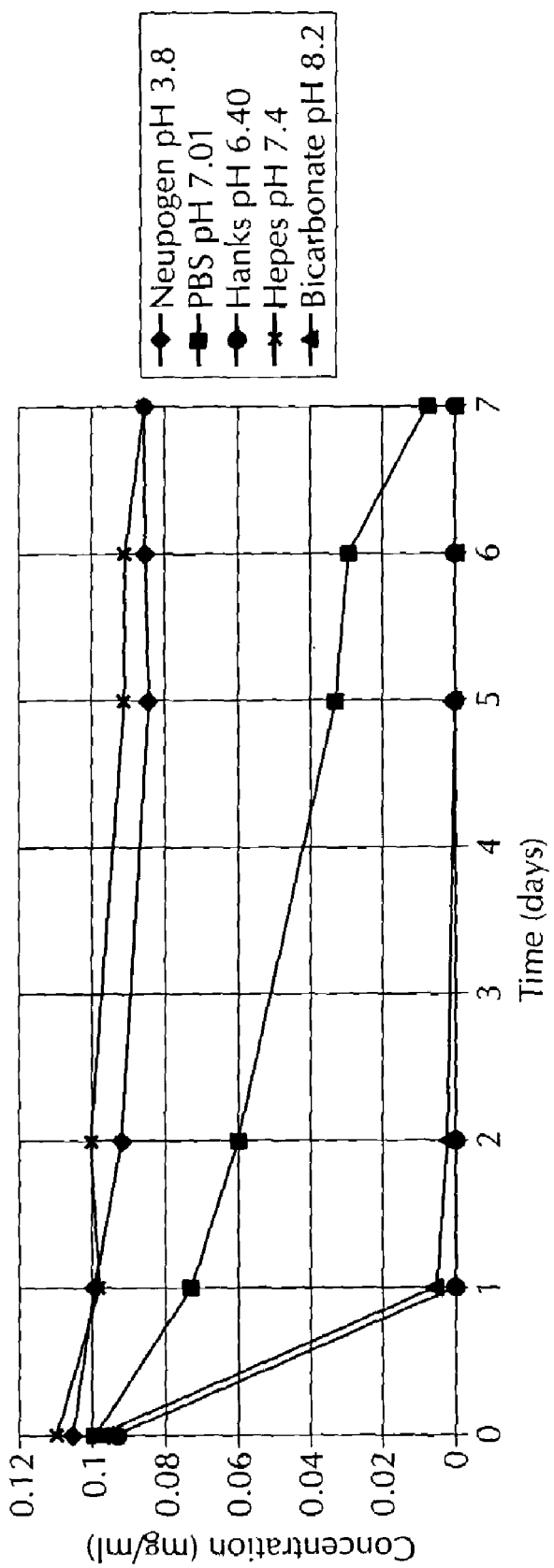
FIG. 8 shows the stability of bG-CSF (concentration in mg/ml) as a function of time in NEUPOGEN® (Filgrastim) buffer (control, pH 4.0), HEPES buffer at pH 7.4, PBS at pH 7.0, Hanks buffer at pH 8.5 and bicarbonate buffer at pH 8.2.

FIG. 8 provides a comparison of the stability of bG-CSF in various buffer systems, including NEUPOGEN® (Filgrastim) (commercially available, USA, human G-CSF), used as a control, HEPES at pH 7.4, PBS at pH 7.0, Hanks buffer (available commercially, USA) and bicarbonate buffer. The results indicate that bG-CSF formulated in 1M HEPES buffer was the most stable of all formulations tested, and exhibited similar stability to the NEUPOGEN® (Filgrastim) buffer at pH 4.0. The stability of bG-CSF in HEPES buffer, as demonstrated in FIG. 8, was surprising and unexpected in that bG-CSF was previously known to be unstable at neutral or physiological pH conditions and at temperatures around 40° C. or greater. The bG-CSF formulated in PBS at pH 7.0, Hanks buffer and bicarbonate buffer was not stable. This was confirmed as described in Table 5.

TABLE 5

| Buffer Solution | Positive Specific Activity (ng/ml) Initials | Positive Specific Activity (ng/ml) 7 days at 40° C.* |
| --- | --- | --- |
| NEUPOGEN ® (Filgrastim) (control, pH 4.0) | 0.01 | 0.1 |
| HEPES (pH 7.4) | 0.01–0.1 | 0.01 to 0.1 |
| PBS (pH 7.0) | 0.1 | 10 |
| Hanks (pH 6.4) | 0.01–1.0 | 100 |
| Bicarbonate (pH 8.2) | 0.1–1.0 | 100–1000 |

*Higher values correspond to lower activity

During 7 days storage at 40° C., bG-CSF in NEUPOGEN® (Filgrastim) and HEPES buffer did not lose any activity. Also shown, bG-CSF in PBS was 10 times less active and bG-CSF in Hanks and Bicarbonate buffer were 100 to 1000 times less active than the initials, respectively.

Figure 9:
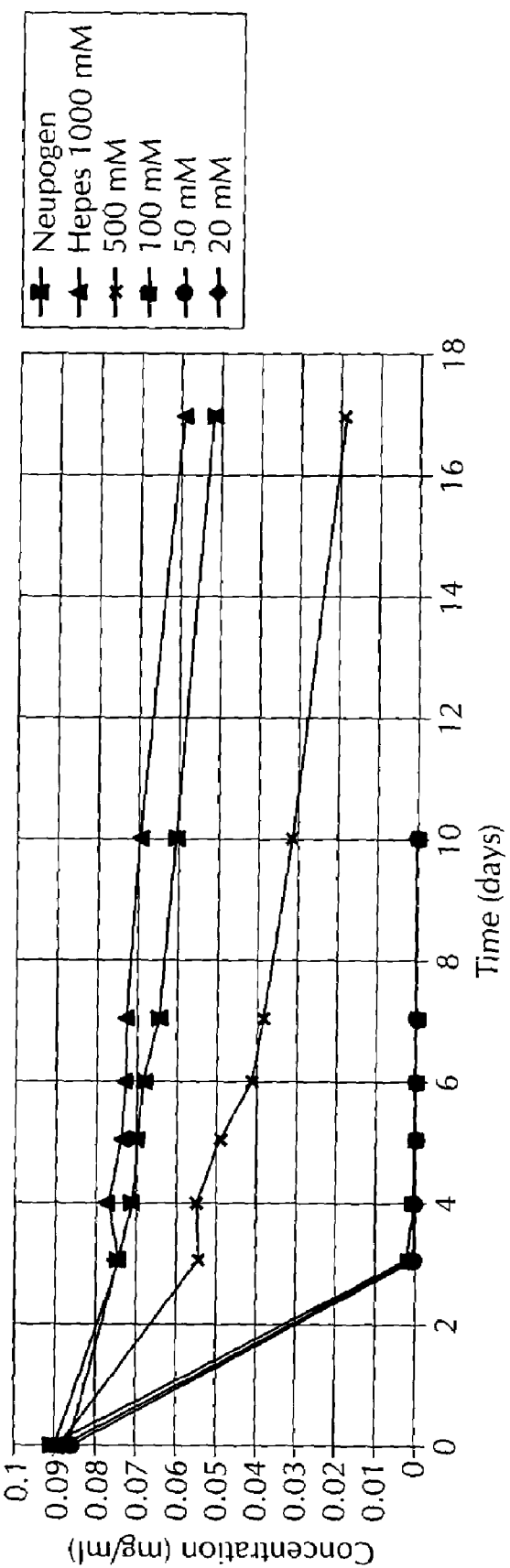
FIG. 9 shows the stability of bG-CSF (concentration in mg/ml) as a function of time in 1000 mM, 500 mM, 100 mM, 50 mM and 20 mM HEPES buffer at 40° C.

FIG. 9 shows the effect of HEPES buffer concentration on the stability of bG-CSF in 1000 mM, 500 mM, 100 mM, 50 mM and 20 mM HEPES buffer at 40° C. As shown in FIG. 9, as the concentration of HEPES was decreased, there was significant loss in stability of bG-CSF.

Figure 10:
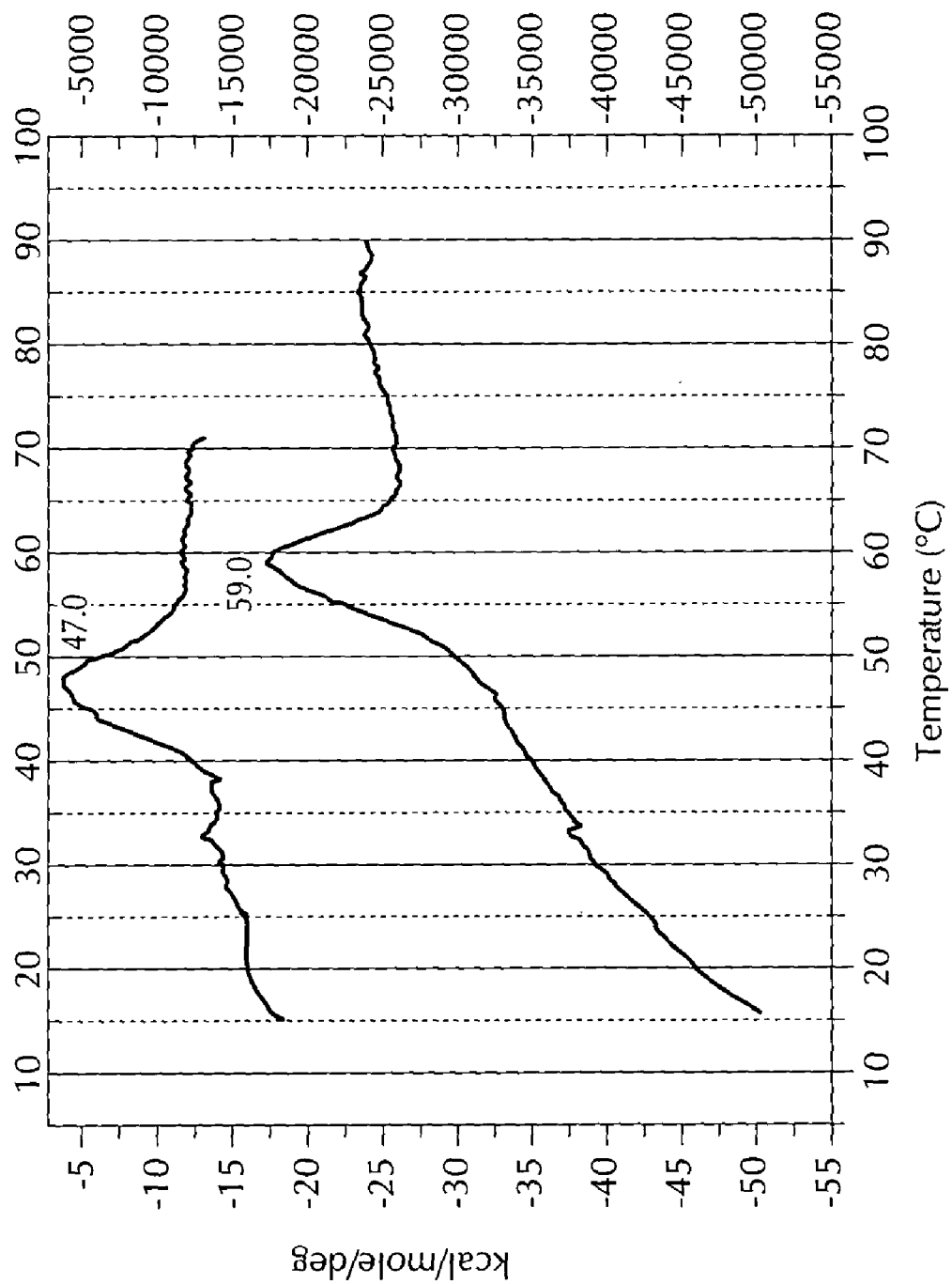
FIG. 10 shows two thermograms (kcal/mole/deg) versus temperature (° C.) for two bG-CSF solutions. The upper thermogram, with a maximum temperature of 47° C., is for bG-CSF formulated in PBS at pH 7.5, and the lower thermogram, with a maximum temperature of 59° C., is for bG-CSF formulated in 1M HEPES at pH 7.5.

FIG. 10 is a thermogram of two different bG-CSF solutions. The upper thermogram, with a maximum temperature of 47° C., is for bG-CSF formulated in PBS at pH 7.5, and the lower thermogram, with a maximum temperature of 59° C., is for bG-CSF formulated in 1M HEPES at pH 7.5. In the absence of HEPES buffer the unfolding temperature of bG-CSF at pH 7.5 is about 40° C. (onset temperature), while bG-CSF in 1M HEPES results in a 10° C. increase in the unfolding temperature. An increase in unfolding temperature is indicative of stabilization.

EXAMPLE 4

In Vivo Performance of bG-CSF Formulated in 1M HEPES

In vivo testing of bG-CSF formulated in 1M HEPES was performed in calves. A 12 µg/kg dose was administered to calves and the white blood cell (WBC) and PMN (neutrophil) numbers monitored. The results are shown in FIG. 11.

Figure 11:
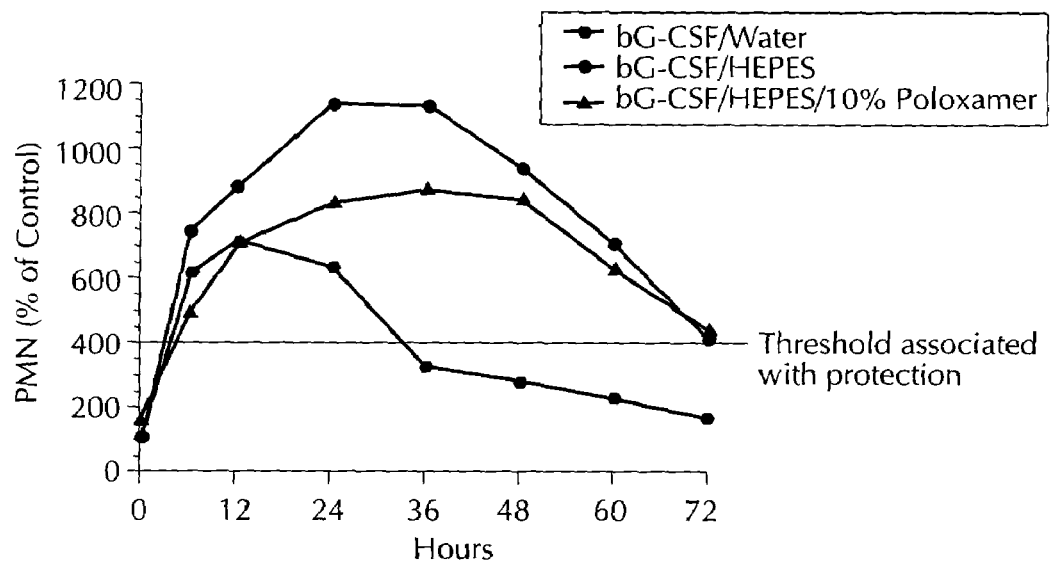
FIG. 11 shows a plot of % PMN (neutrophil) in cattles as a function of time, for three formulations: bG-CSF in water (as a control), bG-CSF in 1M HEPES and bG-CSF in 1M HEPES+10% polaxamer.

FIG. 11, which is a plot of % PMN (neutrophil) versus time, is a comparison of three formulations: bG-CSF in water (as a control), bG-CSF in 1M HEPES and bG-CSF in 1M HEPES+10% polaxamer. As shown in FIG. 11, the PMN numbers stay above the threshold (level associated with protection) for 3 days or 72 hours. Six cattle were tested per formulation.

In a second study, in which a 24 µg/kg dose was administered to calves, using bG-CSF in 1M HEPES buffer+10% polaxamer, a single injection provided approximately 200 hours of protection, or approximately 8 days of coverage. This result demonstrates that HEPES buffer improves the in vivo stability of bG-CSF which in turn, provides for a sustained period of activity, and therefore, delivery of this protein.

EXAMPLE 5

Solubility of bG-CSF in 1M HEPES

Figure 12:
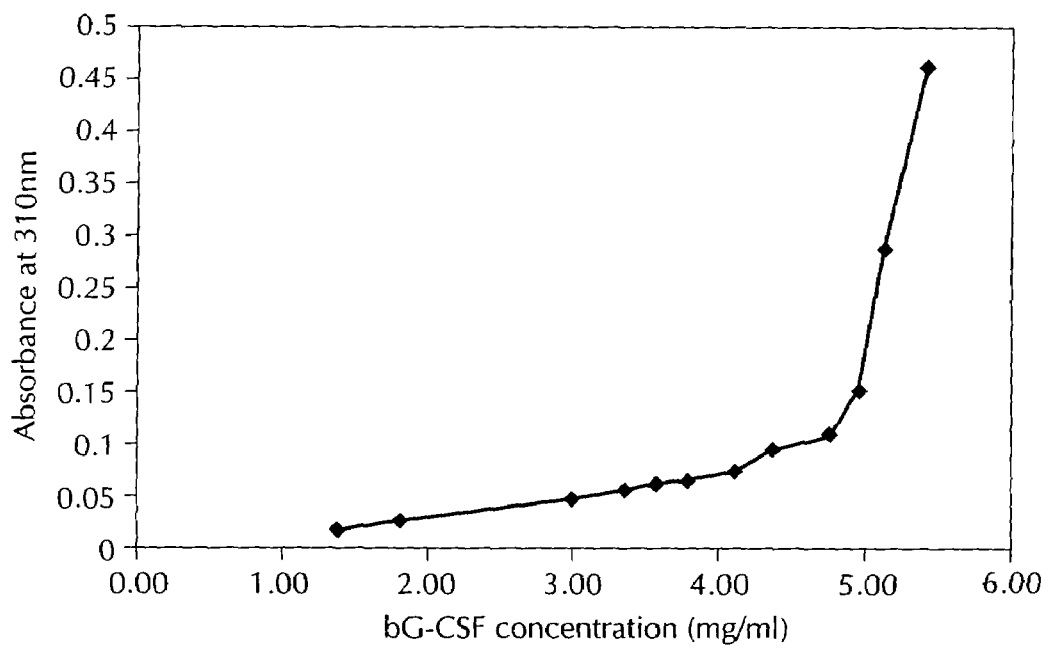
FIG. 12 shows the solubility of bG-CSF in 1M HEPES buffer at pH 7.5 as measured by absorbance at 310 nm versus bG-CSF concentration (mg/ml).

The solubility of bG-CSF in 1M HEPES at pH 7.5 was determined. Approximately 80 mg of bG-CSF was dissolved in 30 ml of 1M HEPES buffer (pH 7.5). The protein solution was filtered through a 0.2 micron GV Millipore filter and then transferred into a 50 ml ultrafiltration cell. The cell was equipped with a low protein binding membrane with a 10,000 molecular weight (MW) cut off. The protein solution was concentrated using the ultrafiltration cell. At various time points samples were removed from the cell for analysis by UV-Vis analysis at 310 nm (measure light scatter) and for concentration by RP HPLC. Absorbance at 310 nm was plotted against concentration. Absorbance at 310 nm should increase linearly with concentration; at saturation there is a sudden break in the curve at 310 nm and the absorbance at 310 nm increases dramatically. The concentration at which this occurs is the maximum solubility. This method is known to those of skill in the art and typically used in determining protein solubility. As shown in FIG. 12, the maximum solubility of bG-CSF in 1M HEPES at pH 7.5 is about 5 mg/ml. The maximum solubility of the protein is shown at the concentration depicting a break in the curve. At a concentration of about 5 mg/ml, there is a sudden increase in absorbance at 310 nm, corresponding to the maximum solubility of the protein.

EXAMPLE 6

Effect of HEPES, TES and TRICINE Buffers on the Unfolding Temperature of bg-CSF

Solutions were prepared containing 0.5 mg/ml bG-CSF in 1M HEPES, 2M HEPES, 1M TES, 2M TES and 1M TRICINE; and 2 mg/ml ml bG-CSF in 1M HEPES, 2M HEPES, 1M TES, 2M TES and 1M TRICINE. These solutions were prepared in the same manner as described in Example 1. A control solution was prepared using PBS (Dulbecco's Phosphate Buffered saline, pH 7.4). The pH of the bG-CSF solutions was pH 7.5. The unfolding temperature of the bG-CSF was determined by differential scanning calorimetry (Microcal Inc, USA) using a scanning rate of 60 degrees per hour at a temperature range of from 20° C. to 90° C. The results are shown in Table 6.

TABLE 6

| bG-CSF concentration | Unfolding Temperature (° C.) | | | | | |
| --- | --- | --- | --- | --- | --- | --- |
| | | HEPES | | TES | | TRICINE |
| (mg/ml) | PBS | 1M | 2M | 1M | 2m | 1M |
| 0.5 | 50.96 | 56.85 | 60.05 | 57.29 | 62.37 | |
| 2 | | 54.94 | 57.62 | 55.23 | 60.49 | 53.68 |

The unfolding temperature was used as a marker of solution stability and in vivo stability for proteins. The results in Table 6 indicate that the unfolding temperature ($T_m$) of bG-CSF formulated in HEPES, TES or TRICINE buffers at concentrations 1 M and higher was significantly higher compared to a PBS control. The three buffers raised the $T_m$ by about 2 to 11° C. The buffer concentration substantially affected the degree of increase in $T_m$. The $T_m$ of bG-CSF increased as the buffer concentration was increased, There was about a 3° C. increase when the HEPES concentration was increased from 1M to 2M, and there was about a 5° C. increase when TES concentration was increased from 1M and 2M. As the bG-CSF concentration was increased, the $T_m$ of bG-CSF decreased There was about a 2° C. decrease when the bG-CSF concentration was increased from 0.5 mg/mL to 2 mg/mL in both HEPES and TES buffers. The TES buffer solution increased the $T_m$ of bG-CSF by over 11° C. at a buffer concentration of 2M and a bG-CSF concentration of 0.5 mg/mL.

The results in Table 6 show that all three buffers (HEPES, TES and TRICINE) significantly increase the $T_m$ of bG-CSF compared to PBS bG-CSF formulated in 2M TES exhibits the highest solution stability relative to other buffers.

EXAMPLE 7

Comparison of the Stability of Human and Bovine G-CSF in PBS and HEPES Formulations Formulations of 0.15 mg/mL hG-CSF and bG-CSF were prepared in Phosphate Buffered Saline (Dulbecco's PBS, pH 7.4), and in 1 M HEPES buffer (1 M HEPES, pH 7.5). The formulations were placed in 1 mL vials (full volume of 400 mL) and stored at 40° C. for 10 days. The samples were assayed every three days by Size Exclusion Chromatography (SEC-HPLC) and visually inspected.

Figure 13:
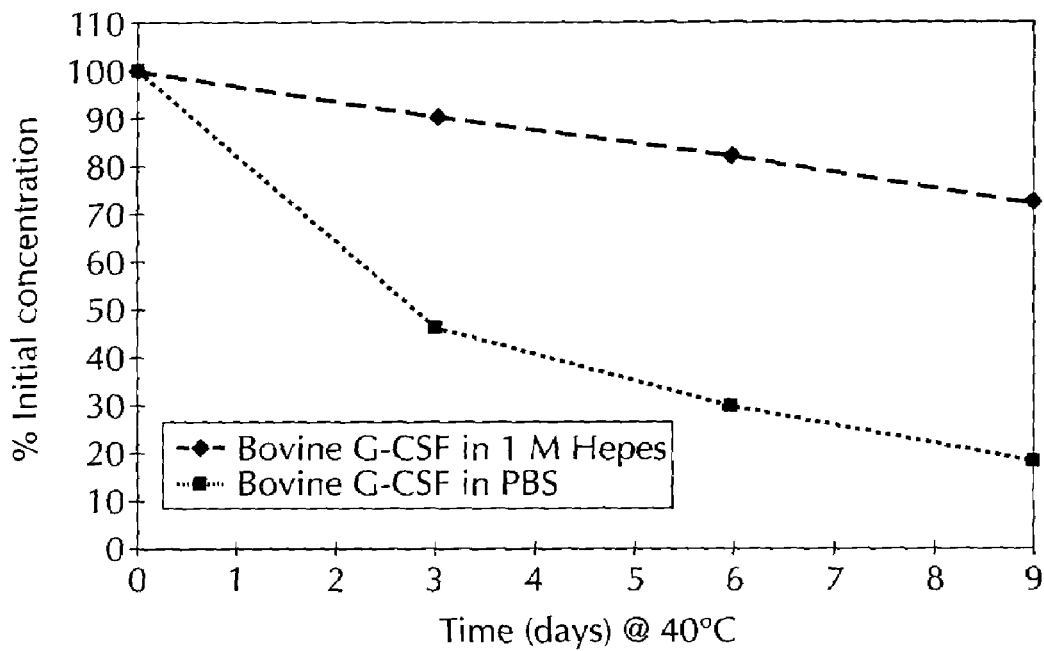
FIG. 13 shows the stability (% initial concentration) of bovine G-CSF in 1M HEPES buffer and in PBS at 40° C.

FIG. 13 shows that a significant improvement was observed in the stability of human G-CSF when formulated in 1 M HEPES buffer, when compared to PBS. Human GCSF exhibited degradation over 10 days at 40° C. when formulated in PBS at pH 7.4, while a 65% recovery was observed when it was formulated in 1 M HEPES buffer.

Figure 14:
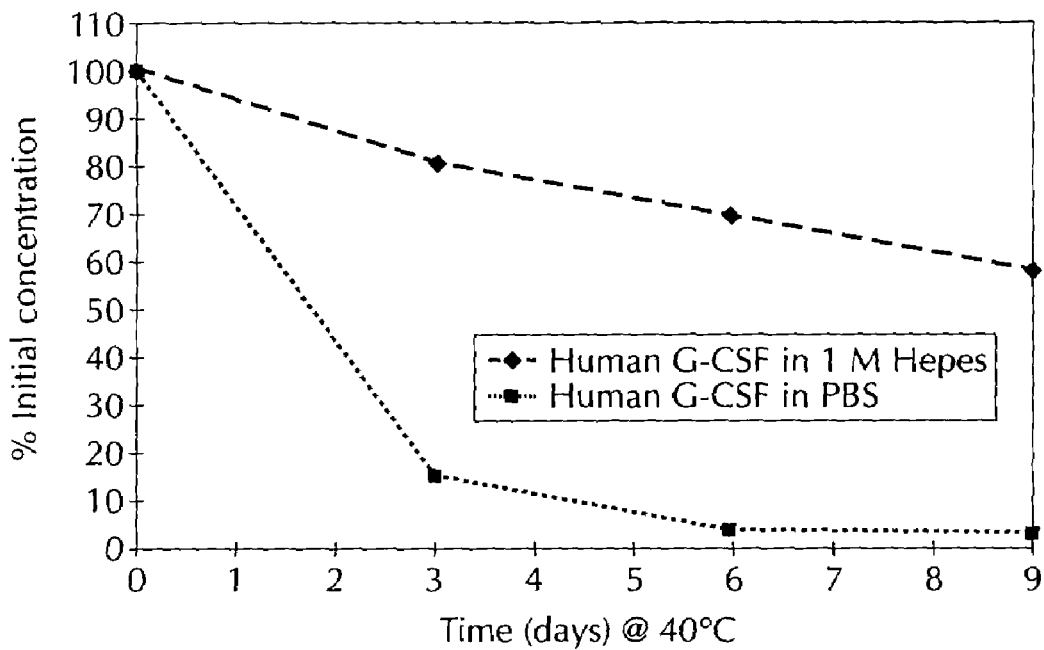
FIG. 14 shows the stability (% initial concentration) of human G-CSF in 1M HEPES buffer and in PBS at 40, C.

FIGS. 13 and 14 show that bovine G-CSF exhibits a somewhat better stability in both HEPES and PBS formulations, than human G-CSF. About an 80% recovery of bovine G-CSF in the 1 M HEPES formulation was observed after 10 days at 40° C., while about a 65% recovery of human G-CSF was observed. Both proteins, bovine and human G-CSF, are substantially more stable in 1 M HEPES buffer, than in PBS.

EXAMPLE 8

Stability of Human and Bovine G-CSF in 1M HEPES Formulations

Formulations of 0.1 mg/mL hG-CSF and bG-CSF were prepared in 1M HEPES buffer (1 M HEPES, pH 7.5). The formulations were placed in 1 mL vials (full volume of 400 □L) and stored at 40° C. for 10 days. The samples were assayed every three days by Size Exclusion Chromatography (SEC-HPLC) and visually inspected.

Figure 15:
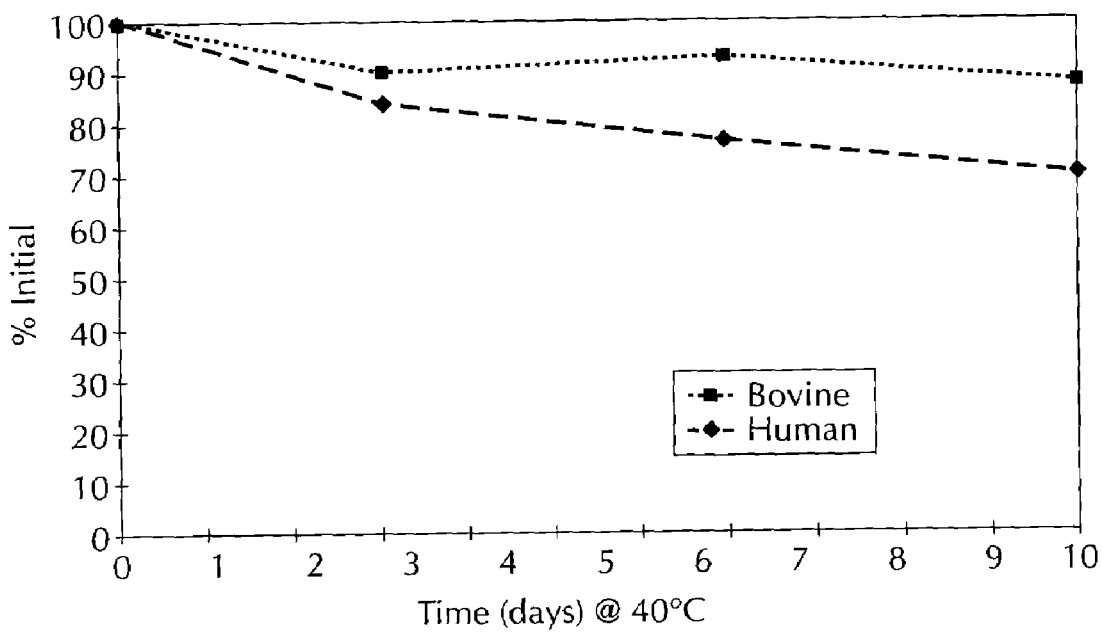
FIG. 15 compares the stability (% initial concentration) of human G-CSF and bovine G-CSF in 1M HEPES buffer at pH 7.5.

FIG. 15 shows the stability of bovine G-CSF and human G-CSF in 1M HEPES formulations. There was about a 90% recovery of bovine G-CSF and about a 70% recovery of human G-CSF after 10 days at 40° C.

EXAMPLE 9

Effect of Formulation pH on bG-CSF Stability

Formulations of 0.1 mg/mL bG-CSF solutions were formulated in 1 M HEPES and 1M Tes buffers at pH 4.0 & 7.5. The formulations were placed into 1 mL vials (full volume of 400 □L) and stored at 40° C. for 10 days. The samples were assayed every three days by Size Exclusion Chromatography (SEC-HPLC).

Figure 16:
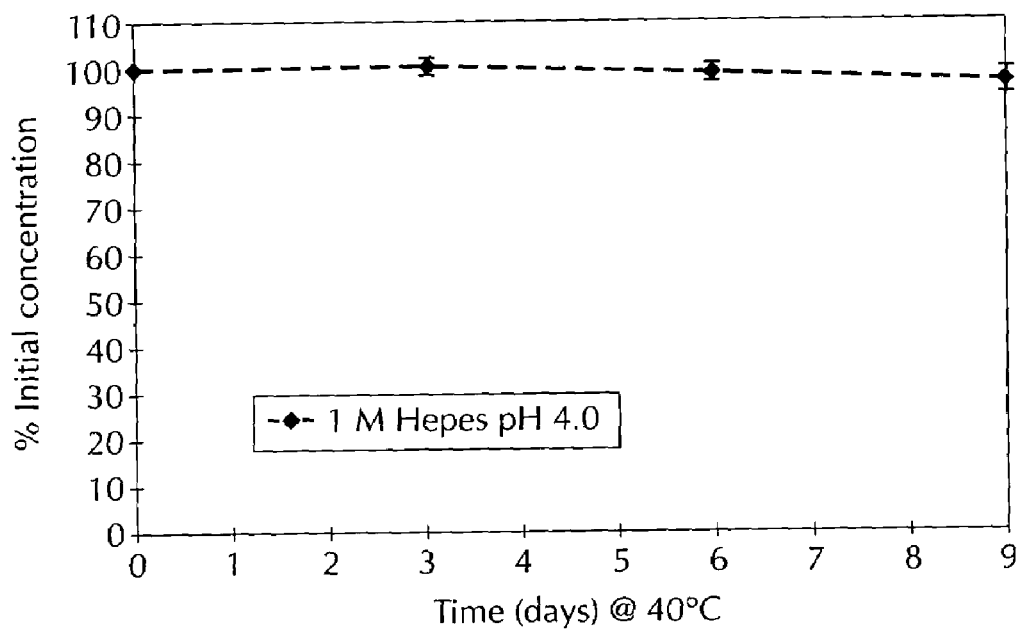
FIG. 16 shows the percent initial concentration of bG-CSF in 1M HEPES buffer at pH 4.0 versus time (days) at 40° C.
Figure 17:
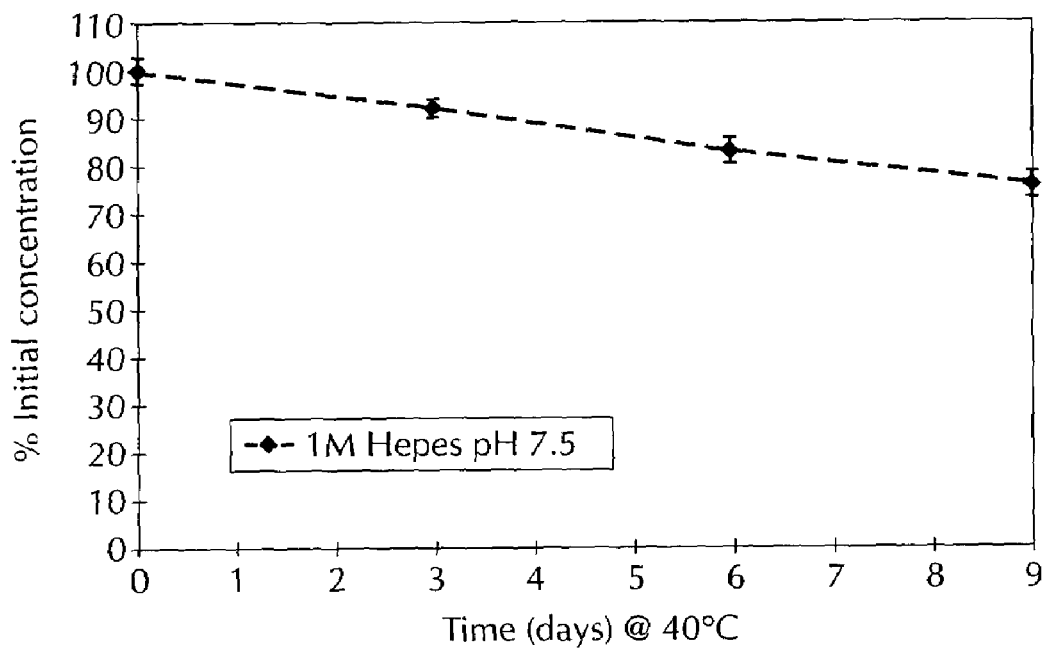
FIG. 17 shows the percent initial concentration of bG-CSF in 1M HEPES buffer at pH 7.5 versus time (days) at 40° C.
Figure 18:
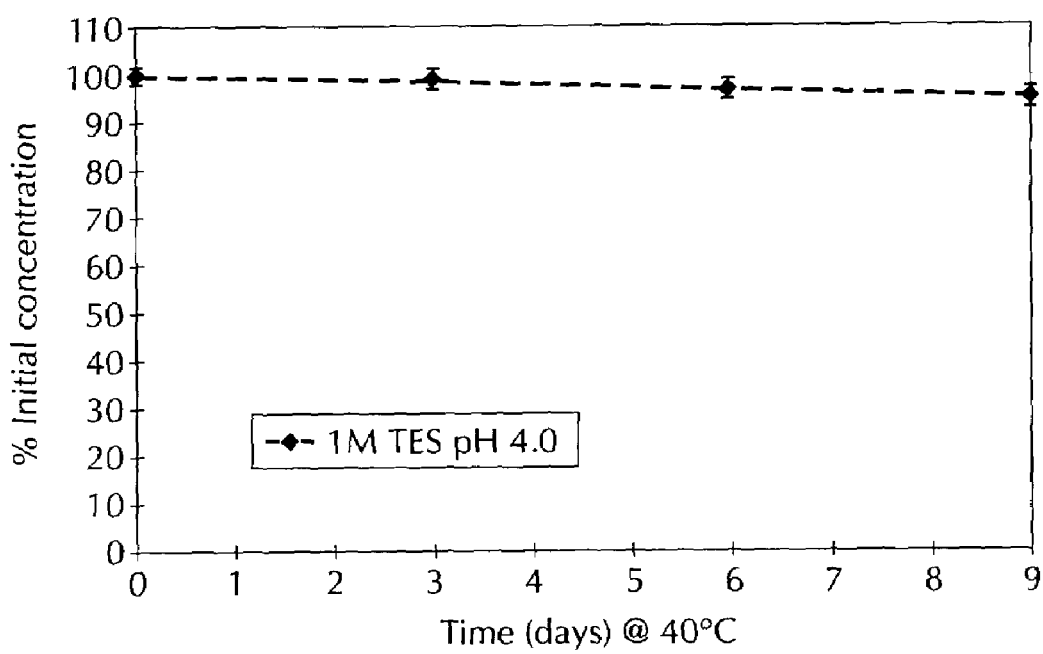
FIG. 18 shows the percent initial concentration of bG-CSF in 1M TES buffer at pH 4.0 versus time (days) at 40° C.
Figure 19:
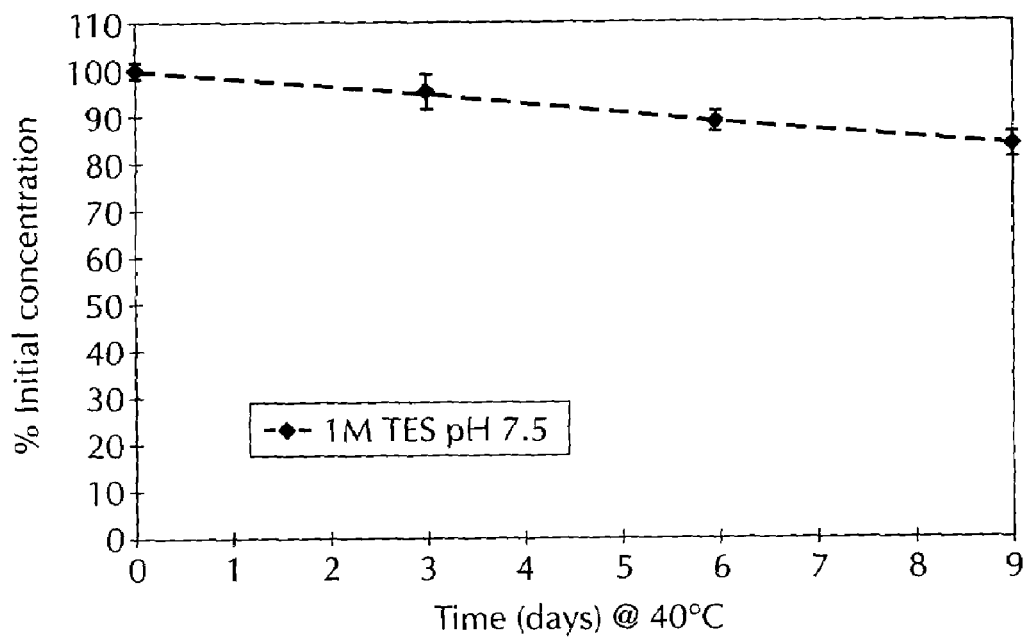
FIG. 19 shows the percent initial concentration of bG-CSF in 1M TES buffer at pH 7.5 versus time (days) at 40° C.

As shown in FIGS. 16 and 18, the bG-CSF recovery after 10 days at 40° C. was about 100% at pH 4.0, compared to FIGS. 17 and 19, which show about an 80–85% recovery observed when the bG-CSF was formulated at pH 7.5.

EXAMPLE 10

Six-Month Sampling of Long-Term Thermal Stability Study of bG-CSF in 1.0 M HEPES and TES Formulations The formulations included in this study are given below. A commercial formulation of 1.0 M HEPES was obtained from GibcoBRL (Lot # 1016436), while 1.0 M Tes was prepared from powder obtained from Fluka Scientific (Lot # RA12602). Buffer pH values were adjusted to 7.5. BG-CSF was provided by Bioprocess (Lot # BP185-11) at a purity of 53.3%.

Formulations were prepared of 0.1 mg/mL and 2.0 mg/mL bG-CSF In 1.0M HEPES and 1.0M TES buffer.

Sample storage employed 3.5 mL Flint Type 1 vials (Lot # R04105-7322) with 13 mm 1888 Gray T/F stoppers (Lot # R05619-7487) using a full volume of 1.0 mL. A summary of sample storage and pull points is given in Table 7. Five vials of each formulation were stored for each assay time point.

TABLE 7

Summary of Sample Storage and Potency Analysis Time Points

| Storage | Initial | 3 Weeks | 6 Weeks | 12 Weeks | 6 Months | 1 Year | 18 Months |
|---|---|---|---|---|---|---|---|
| 5° C. | X | X | X | X | X | X | X |
| 30° C. |  | X | X | X | X | X | X |
| 40° C. |  | X | X | X | X |  |  |

The 2.0 mg/mL bG-CSF formulations were diluted tenfold prior to HPLC analysis.

Figure 20:
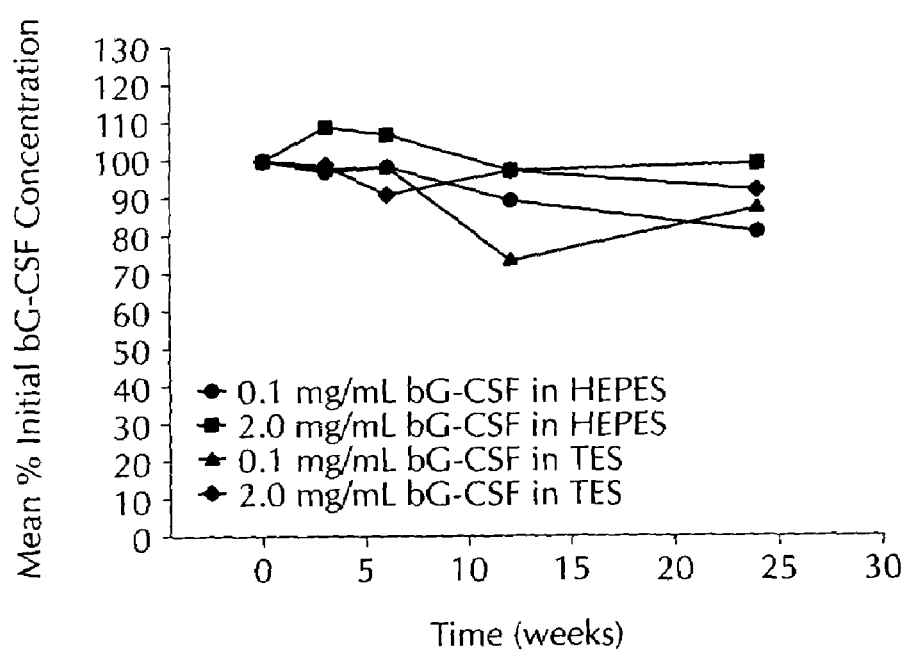
FIG. 20 shows RP HPLC % initial bG-CSF concentration results for samples stored at 5° C. versus time (weeks).
Figure 21:
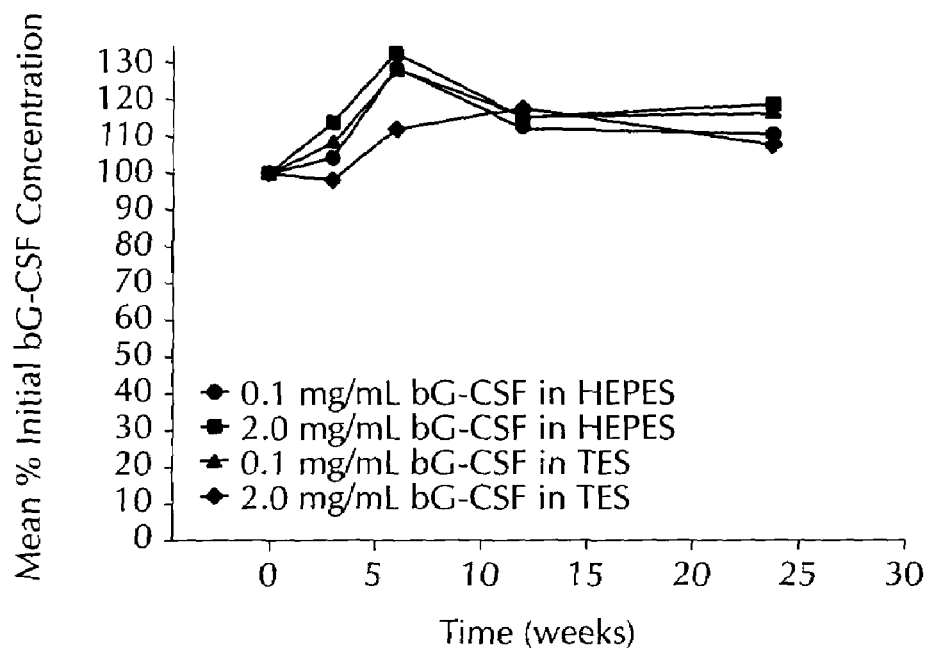
FIG. 21 shows SE HPLC % initial bG-CSF concentration results for samples stored at 5° C. versus time (weeks).
Figure 22:
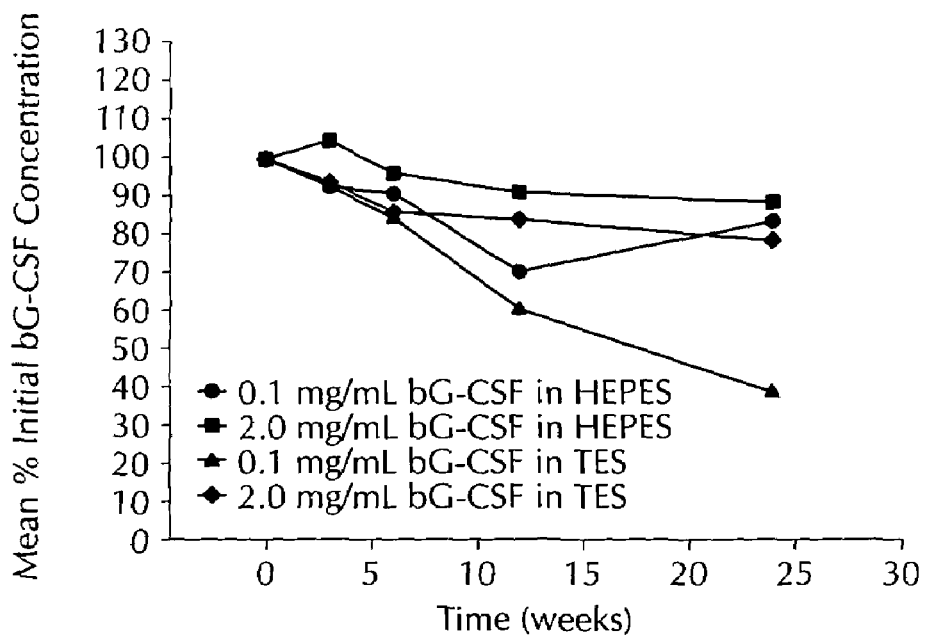
FIG. 22 shows RP HPLC % initial bG-CSF concentration results for samples stored at 30° C. versus time (weeks).
Figure 23:
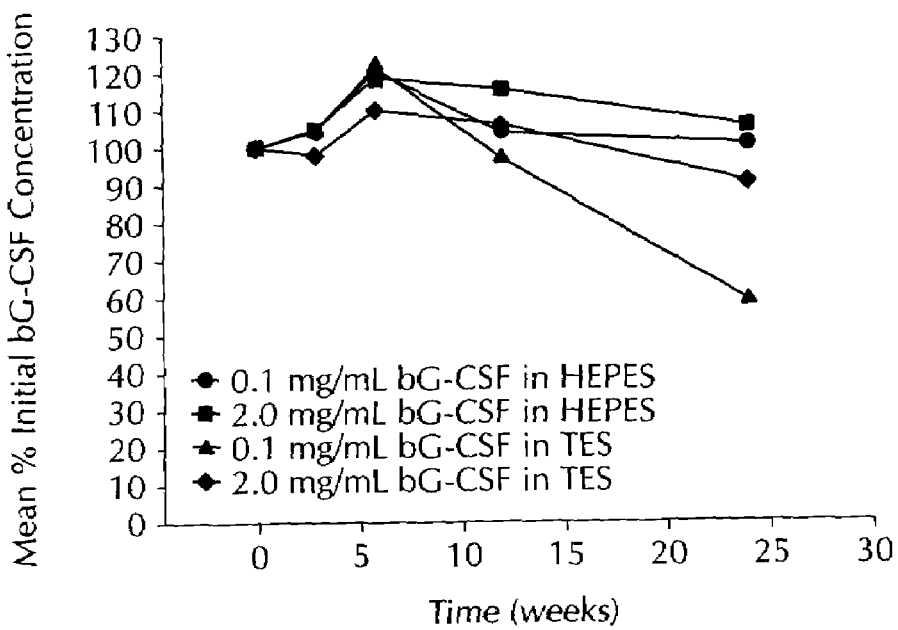
FIG. 23 shows SE HPLC % initial bG-CSF concentration results for samples stored at 30° C. versus time (weeks).
Figure 24:
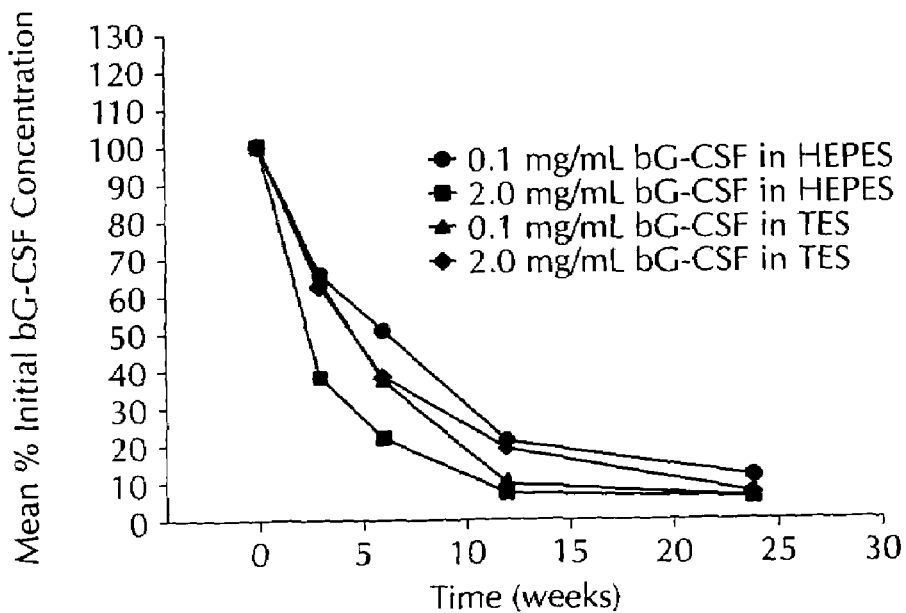
FIG. 24 shows RP HPLC % initial bG-CSF concentration results for samples stored at 40° C.
Figure 25:
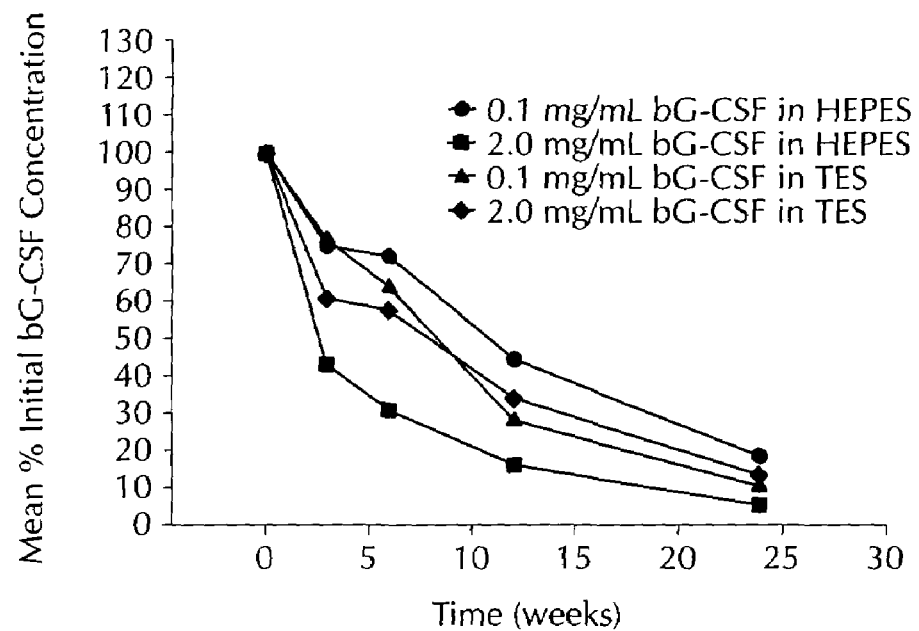
FIG. 25 shows SE HPLC % initial bG-CSF concentration results for samples stored at 40° C. versus time (weeks).

Three samples of each formulation were taken from each storage chamber (5, 30, 40° C.) and assayed by RP and SE HPLC for bG-CSF potency. Each sample was assayed three times. Concentrations were calculated using a standard curve that was previously determined. Percent (%) initial BG-CSF concentrations were determined for each analyses, and a mean was calculated for each formulation at each time point. The mean % initial bG-CSF concentrations were plotted against time for each storage temperature to graphically depict the decrease in bG-CSF potency. FIGS. 20 and 21 are the results obtained by RP and SE HPLC, respectively, for the samples stored at 5° C. The results obtained for the samples stored at 30° C. are given in FIGS. 22 and 23, while those obtained for samples stored at 40° C. can be found in FIGS. 24 and 25.

There was little bG-CSF degradation in samples stored at 5 and 30° C., excluding the 0.1 mg/mL protein formulation in 1.0 M TES.

EXAMPLE 11

Stabilizing Capabilities of HEPES Buffer on Biotherapeutic Proteins

The $T_m$ values of the proteins of interest, discussed below, were determined in both phosphate and HEPES buffers using a MicroCal, Model VP-DSC, microcalorimeter. A 25 mM phosphate buffer solution was prepared using $Na_2HPO_4$ (Lot number 08019 PQ) from Aldrich, and the pH was adjusted to 7.5. 1.0 M HEPES buffer (pH=7.5, Lot number 1016436) was obtained from GibcoBRL. Buffer exchanges were accomplished via a Stirred Ultrafiltration Cell, Model 8010 (Amicon, Inc.), in combination with either a YM10 or YM30 Diaflo® Ultrafiltration Membrane (Amicon, Inc.), depending on the size of the protein.

2.0 mg of lyophilized pST (Lot number 41509-217-2) obtained from Bioprocess was reconstituted in 2.0 mL of Milli-Q water. After five exchanges, 1.0 mL of the reconstituted protein was transferred into 25 mM phosphate buffer using a YM10 membrane. The remaining 1.0 mL was then exchanged into 1.0 M HEPES buffer. Samples were prepared at a 1.0 mg/mL protein concentration and then analyzed by microcalorimetry. Microcalorimetry analysis of pST was performed twice in both phosphate and HEPES buffer.

Approximately 2.0 mL of NIF (Lot number 440631-22-7) was obtained from Bioprocess at a concentration of 2.97. The sample received from Bioprocess were divided into two aliquots. 1.0 ml of the protein was exchanged into 25 mM phosphate buffer, and the remaining NIF was exchanged into 1.0 M HEPES buffer. In each case, five exchanges were employed using a YM30 membrane. Solutions were prepared at a 1.0 mg/mL concentration in the appropriate buffer, and the $T_m$ values were determined via microcalorimetry.

The biotherapeutic proteins that were studied are listed in Table 8 with their respective $T_m$ values that were determined for phosphate and HEPES buffers.

TABLE 8

$T_m$ Results Obtained in the Microcalorimetry Study of Four Biotherapeutic Proteins in Phosphate and HEPES Buffers

| PROTEIN | $T_m$ IN PHOSPHATE | Tm IN HEPES | $VT_m$ |
|---|---|---|---|
| NIF | 59.79 | 63.27 | +3.48 |
| PST | (1) 56.14 | 67.90 | +11.76 |
|  | (2) 54.48 | 63.41 | +8.93 |

Table 8 shows that HEPES buffer provides increased stability for both NIF and pST

EXAMPLE 12

Sustained In-Vivo Activity of Recombinant Bovine Granulocyte Colony Stimulating Factor (rbG-CSF) using HEPES Buffer Bovine Granulocyte Colony Stimulating Factor (bG-CSF) was obtained from Bioprocess Research and Development-Pfizer (Groton, Conn.), mannitol from E. M. Industries (Hawthorne, N.Y.), 1X Dulbecco's Phosphate Buffered Saline (PBS) from GibcoBRL (Grand Island, N.Y.), sodium citrate and sodium acetate from Aldrich (Milwaukee, Wis.), Tween-80, sodium chloride and hydrochloric acid from J.T. Baker (Phillipsburg, USA).

RP-HPLClSize-Exclusion Chromatography (SEC)

Solution stability was monitored by RP-HPLC and SEC. RP-HPLC was performed using a Vydac, Protein C4 column using a mobile phase of 0.1% TFA H2O (Solvent A) and 0.1% TFA CAN (Solvent B). Flow rate: 1 ml/min; UV detection: 220 nm; temperature: 25° C. Size Exclusion Chromatography was performed using a TosoHaas, TSK-GEL $SW_{XL}$, 7.8 mm ID×30 cm column. Mobile Phase: 0.3 M NaCl in 0.05 M citrate buffer pH 5.75; flow rate: 1 ml/min; UV detection: 280 nm; temperature: 25° C.

Microcalorimetry

Denaturation Temperature (TD) was measured using a VP DSC system (MicroCal, Inc.). Approximately 1 ml of the solution was loaded into the cell and run against a reference placebo formulation at a rate of about 10° C./min.

Circular Dichroism

Secondary structure of bG-CSF was monitored using Circular Dichroism Spectroscopy equipped with a temperature scanning measurement accessory (CD*ORD Model J-710/720-Japan Spectroscopic Co., LTD).

Bioassay

In vitro activity of bG-CSF formulations were determined using a murine bone marrow cell proliferation assay (BMC assay). Bone marrow cells were aseptically harvested from the femurs of female CF1 mice (Charles River) by removing the femur and gently flushing the marrow out of the bone using a 3 cc/23 G syringe and Hanks Balanced Salt Solution (Gibco BRL). The cell suspension was filtered through a nylon screen to remove debris and was then centrifuged at 11 OOrpm for ten minutes at room temperature. The supernatant was discarded, and the pellet was resuspended in 15 ml RPM1 medium (Gibco BRL) supplemented with 10% fetal bovine serum (Gibco BRL), 1% penicillinstreptomycin (10,000 units/ml), 1% L-Glutamine (Gibco BRQ. Bone marrow cells were quantitated using a Coulter Channelyzer 256, and the cell concentration was adjusted to yield $6.67 \times 10^5$ cells/ml-. Approximately $10^5$ cells were added to each well of a 96-welled plate. Bovine granulocyte colony stimulating factor formulations were then added to each well (in triplicate) at various concentrations. Following a 3 day incubation at 37° C., (5% $CO_2$) for 3 days, $^3$H-thymidine (New England Nuclear, Boston, Mass.) was added to each well at a final concentration of 2 $\mu$Ci/ml. Radiornetric labeling was allowed to proceed for at least 18 hours at 37° C., (5% $CO_2$). The plates were frozen at −20° C., thawed, and the cells were harvested onto glass 96-well fibermats using a Brandel cell harvester (Biomedical Research and Development Laboratories, Gaithersburg, Md.). Activity was determined using a Wallac 1205 Betaplate liquid scintillation counter (Wallac, Gaithersburg, Md.). Activity of bG-CSF formulations was determined by dividing the sample counts per minute by the media control counts per minute (fold-over-background). Activity of 3 or more fold-over-background was considered positive.

In-Vivo Activity of bG-CSF

In-vivo activity of bG-CSF formulations were tested in young, crossbred beef calves ranging from approximately 100–150 kg body weight. Calves were purchased and shipped to the Animal Health Research Center at Terre Haute, Ind. and acclimated to the facility for a minimum period of two days before allotment to a study. Most calves were used for one study, allowed to rest at least one week, and then reassigned to a second study. Calves were not used for more than two studies. Before allotment to a study calves were pre-screened 1–3 days prior to study initiation by assessing rectal temperature, body weight, general health and total white blood cell (WBC) counts and differentials. In general, calves with rectal temperatures≧104° C. and total WBC counts <4000/mm$^3$> or 12,000/mm$^3$ ~ were excluded from studies. On day 0 calves were bled and weighed before treatment. The dose of 24 µg/kg bG-CSF formulation was calculated at the time of treatment for each calf based on body weight and administered via a subcutaneous injection in the pre-scapular region of the neck. Blood samples were collected in EDTA anticoagulant for WBC/differential via venipuncture from the neck at pre-determined times after treatment. Total WBC counts were performed on a Nova Celltrak 1 hematology cell counter using a 1:250 dilution of whole blood in isotonic diluent. Differential WBC counts were performed using dried blood smears stained with a Diff-Quik stain set (Dade). A total of 100 WBCs were counted and differentiated on a Zeiss light-microscope with a 100× oil immersion lens and 12.5× ocular eyepieces (total magnification=1250×).

Effect of pH and Temperature on the Solution Stability of bG-CSF

Table 9 shows the effect of temperature on the stability of bG-CSF. The impact of temperature on the solution stability of bG-CSF was followed by RP-HPLC, SEC-HPLC, bioassay, and visual inspection (formulation: 0.1 mg/ml bG-CSF, 5% mannitol, 10 mM acetate buffer, 0.004% between-80, pH 4.0. As seen from Table 9, there is a discontinuity in the stability of bG-CSF at temperatures at or above 40° C. By both RPHPLC and SEC-HPLC there is a loss of the parent protein peak at 40° C. and above. The disappearance of the parent peak at higher temperatures is followed by an increase in particulates in the solution. This was observed both visually and by monitoring light scatter at 310 nm. Bovine G-CSF solutions stored at 40° C. for 3 weeks are 10–100 times less active than at 5° C. and 30° C. At 50° C. for 3 weeks, bG-CSF is 100–1000 times less active than solutions stored at 5 and 30° C.

TABLE 9

The Stability of bG-CSF as function of temperature (3 week stability).

| Temperature (° C.) | RP-HPLC (% of initial) | SEC-HPLC (% of initial) | Visual Inspection by Tyndall Beam (Light Scatter Abs. @ 310 nm) | Positive Specific Activity (ng/ml in BMC assay)* |
|---|---|---|---|---|
| 5 | 88.5 | 97.6 | Clear (0.2 au) | 0.1–1 |
| 30 | 67.3 | 76.8 | Clear (0.04 au) | 01.–1 |
| 40 | 5.6 | 5.4 | Slightly cloudy (>0.1 au) | 10–100 |
| 50 | 1.9 | No parent peak | Cloudy (>0.1 au) | 100-1000 |

*Activity tested in mouse BMC assay (Note: higher numbers indicate less activity).

Figure 26:
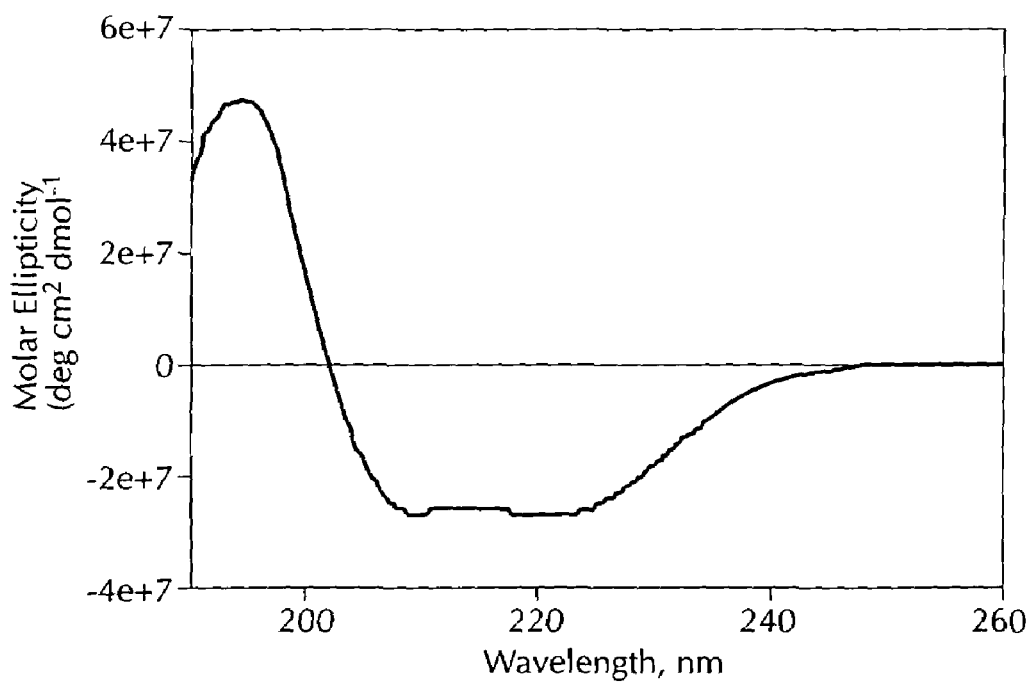
FIG. 26 is the CD (circular dichroism) spectrum of bG-CSF.
Figure 27:
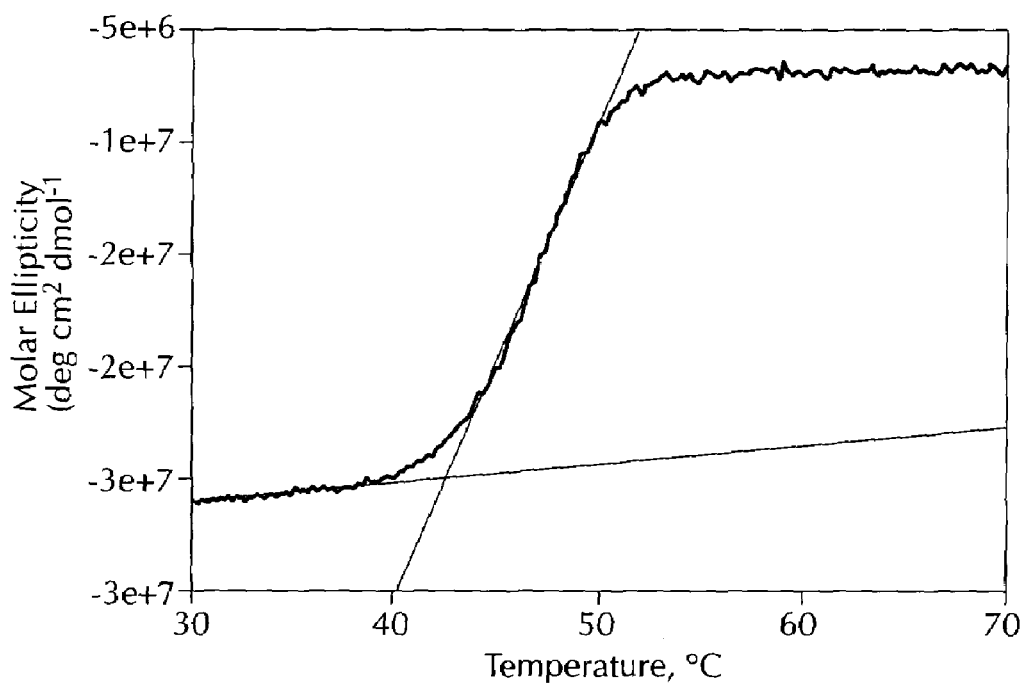
FIG. 27 is a plot of molar ellipticity at a wave length of 222 nm as a function of temperature.

Circular dichroism (CD) was used to follow the impact of temperature on bG-CSF. The CD spectrum of bG-CSF is illustrated in FIG. 26. The spectrum suggests that the secondary structure of bG-CSF is mostly a-helix, similar to human G-CSF, which is structurally very similar to bG-CSF. The CD spectra were examined at various temperatures in order to determine the denaturation temperature (TD). FIG. 27 is a plot of molar ellipticity at wavelength of 222 nm (characteristic wavelength for a-helix) as a function of temperature. Between 40° C. and 50° C., the molar ellipticity increases, indicating the loss of secondary structure and the denaturation of bG-CSF.

The effect of pH on the solution stability of bG-CSF was also assessed. In order to delineate only the effect of pH on stability and not the impact of denaturation due to temperature, the solutions were stored at 30° C. (TD of bG-CSF between 40–50° C.). Table 10 summarizes the stability of bG-CSF as a function of pH over a 2 week period at 30° C. The rate of protein activity loss increases as pH increases. The data suggests that at low pH, the cysteine in bG-CSF is protonated, and hence the formulation is more stable. At high pH, this free cysteine is involved in disulfide exchange reactions and are the likely cause for instability.

TABLE 10

The Stability of bG-CSF as a function of pH (2 week stability at 30° C.).

| pH | RP-HPLC (% of initial) | SEC-HPLC (% of initial) | Visual Inspection by Tyndall Beam | Positive Specific Activity (ng/ml in BMC assay)* |
|---|---|---|---|---|
| 4.0 | 96.5 | 100 | Clear solution | 1–10 |
| 5.0 | 91.9 | 90.1 | Clear solution | 10–100 |
| 6.0 | 75.2 | 84.6 | Tiny particulates | 100 |
| 7.0 | 30.5 | 45.7 | Long gelatinous particles | 100–1000 |

*Activity tested in mouse BMC assay (Note: higher numbers indicate less activity).

Effect of HEPES Buffer on bG-CSF Solution Stability

Figure 28:
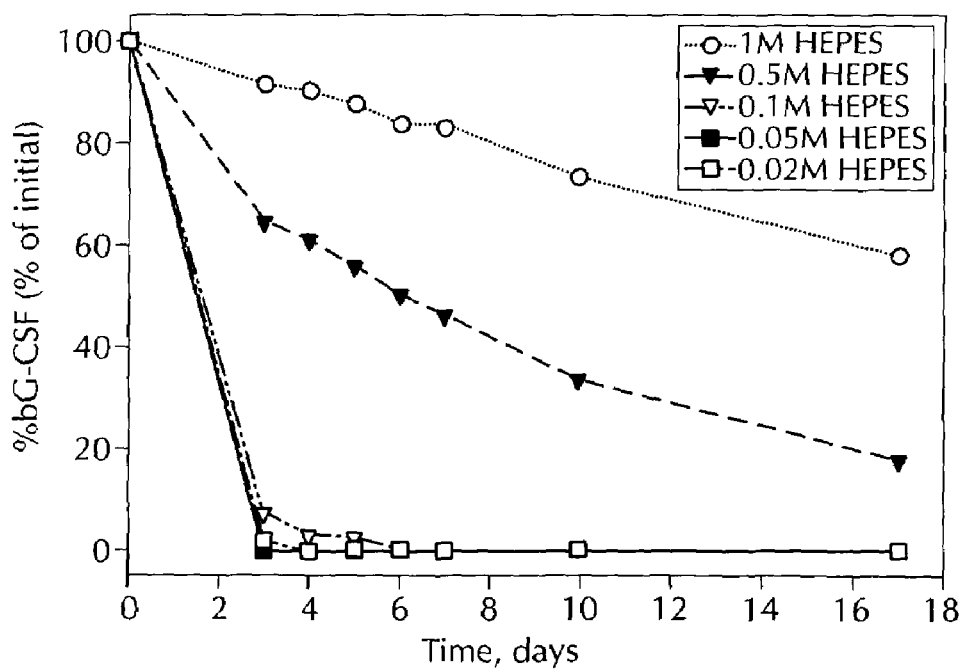
FIG. 28 shows the percent initial concentration of bG-CSF in various concentrations of HEPES buffer at pH 7.5 at 40° C. versus time (days).

We have observed that bG-CSF formulated in 1 M HEPES buffer at pH 7.5 exhibited greater solution stability even when stored at 40° C. for several days. This was unexpected since it is previously known that bG-CSF is unstable at neutral pH and denatures at temperatures at or above 40° C. FIG. 28 illustrates the effect of HEPES buffer concentration on the solution stability of bG-CSF at pH 7.5 and storage temperature of 40° C. The stability of bG-CSF decreased significantly as the concentration of HEPES buffer was decreased. The effect of 1 M HEPES on the denaturation temperature (TD) of bG-CSF was determined by microcalorimetry. FIG. 10, a thermogram, compares the two formulations (with and without 1M HEPES) on the TD of bG-CSF. In the absence of HEPES buffer the onset of the endothermic transition is about 40° C., while bG-CSF formulated in 1 M HEPES buffer has a TD onset of around 50° C. An increase in denaturation temperature is usually indicative of stabilization.

In-Vivo Activity of bG-CSF

Figure 29:
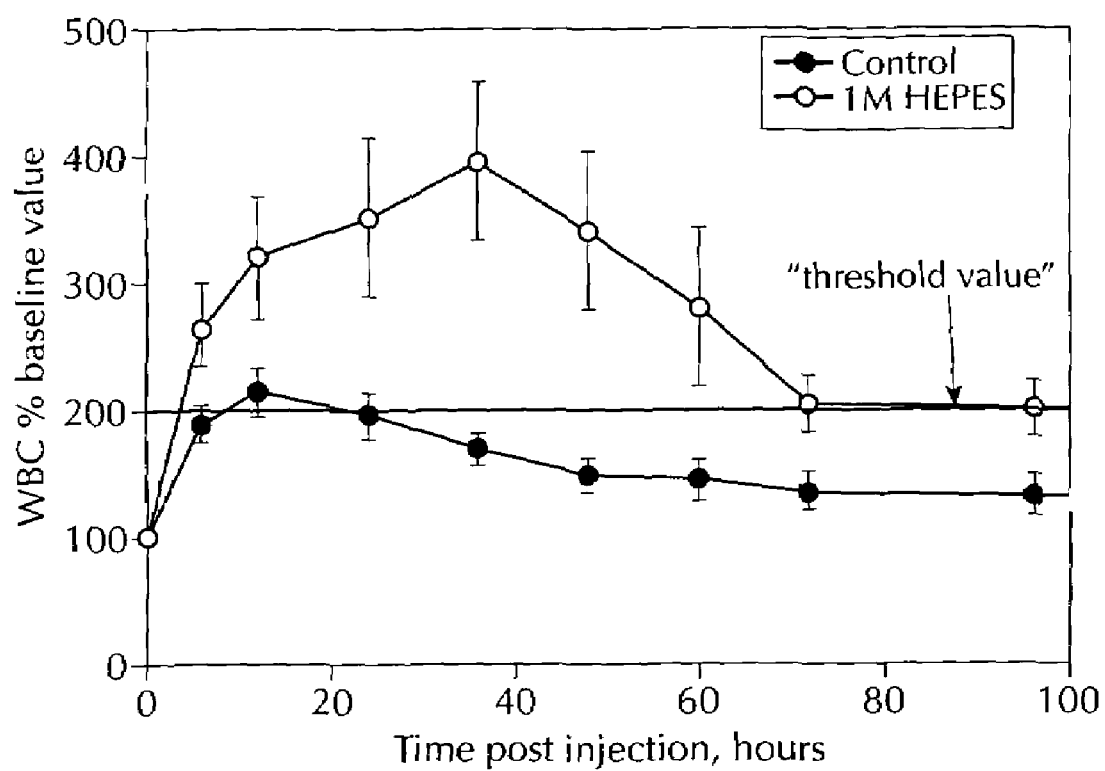
FIG. 29 is a plot of WBC versus time past injection (in hours) for bG-CSF formulated in 1M HEPES versus a control formulation.

We evaluated the in-vivo activity of this formulation in cows. FIG. 29, which is a plot of WBC count versus time, is a comparison of bG-CSF formulated in 1M HEPES compared to the "control" formulation. "Control" refers to the formulation containing 5% mannitol, 10 mM acetate buffer, between-80, pH 4.0.

As seen in FIG. 29, the VBC count stay above threshold value of 200% baseline level (level associated with protection against infections) for only about 24–30 hours. However, when bG-CSF was formulated in 1 M HEPES the PMN numbers remain above threshold for a minimum of 3 days or 72 hours (in some cases the VVTC remained above threshold for almost a week). This study was reproducible (in each study 6 cows per formulation were used). The results of this study suggest that HEPES buffer is not only serving as a stabilizer in vitro, but is somehow improving the in-vivo performance of bG-CSF.

The unexpected results observed with HEPES buffer on bG-CSF performance prompted the investigation of similar buffers such as MOPS, HEPPS, TES, and TRICINE. These buffers also exhibited an improved in-vitro stability of bG-CSF similar to the HEPES buffer. An in-vivo study was conducted where bG-CSF was formulated in TES buffer and Tricine buffer, both formulations resulted in an extended in vivo activity of bG-CSF in cows, similar to the HEPES formulation.

Formulating bG-CSF in 1M HEPES buffer results in sustained activity of bG-CSF in vivo. This sustained activity may be as a result of improved stability of bG-CSF at the injection site. Solution stability of bG-CSF at neutral pH and temperature of 40, C was significantly improved when bG-CSF was formulated in 1 M HEPES. Other organic buffers, such as MOPS, HEPPS, TES, and Tricine, also resulted in an improvement in the stability of bG-CSF.

What is claimed is:

1. A stabilized protein composition consisting of a granulocyte colony stimulating factor (G-CSF) and a stabilizing buffer selected from the group consisting of N-2-hydroxyethylpiperazine-N'-2-aminoethane sulfonic acid (HEPES), N-tris-(hydroxymethyl)methyl-2-aminoethane sulfonic acid (TES), N-tris(hydroxymethyl) methylglycine (Tricene), 2-(N-morpholino)ethane sulfonic acid (MES), bis-(2-hydroxyethyl)imino-tris-(hydroxymethyl)methane (bis-tris), N-2-acetamidoiminodiacetic acid (ADA), N-(2-acetamido) iminodiacetic acid (ACES), piperazine-N,N'-bis (2-ethanesulfonic acid) (PIPS), 3-(N-morpholine)-2-hydroxypropane sulfonic acid (MOPSO), 1,3-bis[tris(hydroxymethyl)methylamino]propane(bis-tris propane), N,N-bis-( 2-hydroxyethyl)-2-aminoethane sulfonic acid (BES), 3-(N-morpholine)propane sulfonic acid (MOPS), 3-[N-bis(hydroxyethyl)-amino]-2-hydroxypropane sulfonic acid (DIPSO), 3-[N-(tris-hydroxymethyl)methylamino]-2-hydroxypropane sulfonic acid (TAPSO), piperazine-N,N'bis-(2-hydroxypropane) sulfonic acid (POPSO), N-hydroxyethylpiperazine-N'-2-hydroxypropane sulfonic acid (HEPPSO), N-2-hydroxyethylpiperazine-N'-2-aminopropane sulfonic acid (EPPS), N,N-bis-(2-hydroxyethyl)glycine (bicine), N-tris(hydroxymethyl)methyl-3-aminopropane sulfonic acid (TAPS), 3-N-($\alpha$,$\alpha$-dimethylhydroxuethyl)-amino-2-hydroxypropane sulfonic acid (AMPSO) and 3-N-cyclohexylamino sulfonic acid (CAPSO), wherein said composition maintains therapeutic levels of said protein for a sustained period, and said protein is present in an amount sufficient to provide therapeutic benefit to a mammal for a predetermined period of time.

2. The composition of claim 1 wherein the composition is at a physiological pH.

3. The composition of claim 1 wherein the composition is at a pH of from about 4.0 to about 7.5.

4. The composition of claim 1 wherein the composition is at a physiological temperature.

5. The composition of claim 1, wherein the sustained period is at least three days.

6. The composition of claim 1 wherein the sustained period is at least three days in vivo.

7. The composition of claim 1 wherein said G-CSF is selected from the group consisting of human granulocyte colony stimulating factor (G-CSF), bovine G-CSF and canine G-CSF.

8. The composition of claim 7 wherein the G-CSF is present at a concentration in the range of 0.01 to 5 mg/ml.

9. The composition of claim 1 or 7 wherein the stabilizing buffer is present in a concentration ranging from about 1.0M to about 2M.

10. The composition of claim 7 wherein the stabilizing buffer is HEPES and is present in a concentration of about 1M.

11. A pharmaceutically acceptable dosage form of a stabilized protein composition for parenteral administration to a mammal, consisting of a granulocyte colony stimulating factor (G-CSF) and a pharmaceutically acceptable stabilizing buffer selected from the group consisting of: HEPES, TES, Tricine, MES, bis-tris, ADA, ACES, PIPS, MOPSO, bis-tris propane, BES, MOPS, DIPSO, TAPSO, POPSO, HEPPSO, EPPS, bicine, TAPS, AMPSO and CAPSO, wherein said composition maintains therapeutic levels of said protein for a sustained period, said protein is present in an amount sufficient to provide therapeutic benefit to a mammal for a predetermined period of time.

12. The pharmaceutically acceptable dosage form of claim 11 wherein said G-CSF is bovine G-CSF present at a concentration in the range of about 0.01 to 5 mg/ml, the stabilizing buffer is selected from the group consisting of HEPES, TES and TRICINE, the mammal is a cow, the predetermined period of time is at least 3 days and; the composition is at a pH of about 7.5.

13. The pharmaceutically acceptable dosage form of claim 12 wherein the buffer is HEPES, wherein the HEPES is present at a concentration ranging from about 1.0M to about 2M.

14. The pharmaceutically acceptable dosage form of claim 13 wherein the bovine G-CSF is administered in a dose in the range of from about 0.1 $\mu$g/kg.

15. A stabilized protein composition consisting of bovine G-CSF and HEPES buffer, which composition provides for an extended shelf life in the range of from about 3 weeks to about 18 months.

16. The composition of claim 15 wherein the HEPES buffer is in a concentration ranging from about 0.05M to about 2M, and the composition is at a pH of about 7.5.

17. The composition of claim 16 wherein the composition temperature is about 4° C.

18. A method of preparing a pharmaceutically acceptable dosage form of a stabilized protein composition for parenteral administration to a mammal, comprising the step of combining a granulocyte colony stimulating factor (G-CSF) and a stabilizing buffer selected from the group consisting of HEPES, TES, Tricine, MES, bis-tris, ADA, ACES, PIPS, MOPSO, bis-tris propane, BES, MOPS, DIPSO, TAPSO, POPSO, HEPPSO, EPPS, bicine, TAPS, AMPSO and CAPSO, wherein the stabilized protein composition maintains therapeutic levels of the protein for a sustained period, and wherein the protein is present in an amount sufficient to provide protection to a mammal for at least three days.

* * * * *